(12) United States Patent
Chitre et al.

(10) Patent No.: US 11,214,536 B2
(45) Date of Patent: Jan. 4, 2022

(54) POLYMORPHS AND USES THEREOF

(71) Applicant: Inspirna, Inc., New York, NY (US)

(72) Inventors: Saurabh Chitre, Bonnyrigg (GB); Hayley Reece, Dalkeith (GB); Stephen Wald, Woodcliff Lake, NJ (US)

(73) Assignee: Inspirna, Inc., New York, NY (US)

( * ) Notice: Subject to any disclaimer, the term of this patent is extended or adjusted under 35 U.S.C. 154(b) by 0 days.

(21) Appl. No.: 16/765,532

(22) PCT Filed: Nov. 20, 2018

(86) PCT No.: PCT/US2018/062063
§ 371 (c)(1),
(2) Date: May 20, 2020

(87) PCT Pub. No.: WO2019/104062
PCT Pub. Date: May 31, 2019

(65) Prior Publication Data
US 2020/0317605 A1    Oct. 8, 2020

Related U.S. Application Data

(60) Provisional application No. 62/589,161, filed on Nov. 21, 2017.

(51) Int. Cl.
*C07C 229/34* (2006.01)
*A61K 47/10* (2017.01)
*A61K 47/12* (2006.01)
*A61K 47/18* (2017.01)

(52) U.S. Cl.
CPC ............ *C07C 229/34* (2013.01); *A61K 47/10* (2013.01); *A61K 47/12* (2013.01); *A61K 47/183* (2013.01)

(58) Field of Classification Search
CPC ...... C07C 229/34; A61K 47/10; A61K 47/12; A61K 47/183
See application file for complete search history.

(56) References Cited

U.S. PATENT DOCUMENTS

| | | |
|---|---|---|
| 4,683,202 A | 7/1987 | Mullis |
| 5,215,882 A | 6/1993 | Bahl et al. |
| 5,223,409 A | 6/1993 | Ladner et al. |
| 5,324,731 A | 6/1994 | Kaddurah-Daouk et al. |
| 5,530,101 A | 6/1996 | Queen et al. |
| 5,565,332 A | 10/1996 | Hoogenboom et al. |
| 5,585,089 A | 12/1996 | Queen et al. |
| 5,639,641 A | 6/1997 | Pedersen et al. |
| 5,676,978 A | 10/1997 | Teicher et al. |
| 5,707,807 A | 1/1998 | Kato |
| 5,807,522 A | 9/1998 | Brown et al. |
| 5,837,832 A | 11/1998 | Chee et al. |
| 5,843,974 A | 12/1998 | Swift |
| 5,958,342 A | 9/1999 | Gamble et al. |
| 5,994,076 A | 11/1999 | Chenchik et al. |
| 6,004,755 A | 12/1999 | Wang |
| 6,040,138 A | 3/2000 | Lockhart et al. |
| 6,048,695 A | 4/2000 | Bradley et al. |
| 6,060,240 A | 5/2000 | Kamb et al. |
| 6,087,112 A | 7/2000 | Dale |
| 6,090,556 A | 7/2000 | Kato |
| 6,316,503 B1 | 11/2001 | Li et al. |
| 6,652,860 B1 | 11/2003 | Singh et al. |
| 6,716,622 B2 | 4/2004 | Curiel et al. |
| 6,906,069 B1 | 6/2005 | Li et al. |
| 7,135,575 B2 | 11/2006 | Munson et al. |
| 7,183,295 B2 | 2/2007 | Yamazaki et al. |
| 7,247,748 B2 | 7/2007 | Thompson et al. |
| 7,365,085 B2 | 4/2008 | Bhat et al. |
| 7,476,519 B2 | 1/2009 | Monforte |
| 7,560,586 B2 | 7/2009 | Thompson et al. |
| 7,576,215 B2 | 8/2009 | Collini et al. |
| 7,741,317 B2 | 6/2010 | Chao et al. |
| 7,790,745 B2 | 9/2010 | Yang et al. |
| 7,799,782 B2 | 9/2010 | Munson et al. |
| 7,897,750 B2 | 3/2011 | Monforte |
| 7,998,995 B2 | 8/2011 | Boren et al. |
| 8,039,493 B2 | 10/2011 | Dehmlow et al. |
| 8,236,753 B2 | 8/2012 | Blacklow et al. |
| 8,257,750 B2 | 9/2012 | Ranganathan |
| 8,324,367 B2 | 12/2012 | Kaemmerer et al. |
| 8,357,679 B2 | 1/2013 | Cooke et al. |
| 8,993,628 B2 | 3/2015 | Forman et al. |
| 9,399,028 B2 | 7/2016 | Tavazoie et al. |

(Continued)

FOREIGN PATENT DOCUMENTS

| | | |
|---|---|---|
| AU | 1552599 A | 7/1999 |
| AU | 2003222083 A1 | 10/2003 |

(Continued)

OTHER PUBLICATIONS

Morissette et al. in Advanced Drug Delivery Reviews 56 (2004) 275-300 (Year: 2004).*
Definition of Cancer' at MedicineNet.com at https://web.archive.org/web/20120807164825/http://www.medterms.com/script/main/art.asp?articlekey=2580) (Year: 2012).*
Sausville et al. Cancer Research, 2006, vol. 66, pp. 3351-3354 (Year: 2006).*
Johnson et al. British J. of Cancer, 2001, 84(10):1424-1431 (Year: 2001).*

(Continued)

*Primary Examiner* — Dennis Heyer
(74) *Attorney, Agent, or Firm* — Clark & Elbing LLP

(57) ABSTRACT

The present invention relates to new polymorphs of LXRβ agonists which exhibit improved physical properties. The invention also relates to pharmaceutical compositions including a pharmaceutically effective amount of an LXRβ agonist, as well as methods of treating cancer including administration of a formulation including an LXRβ agonist to a subject in need thereof.

9 Claims, 11 Drawing Sheets

(56) References Cited

U.S. PATENT DOCUMENTS

| | | |
|---|---|---|
| 9,421,218 B2 | 8/2016 | Hernando et al. |
| 9,526,710 B2 | 12/2016 | Tavazoie et al. |
| 9,707,195 B2 | 7/2017 | Tavazoie et al. |
| 9,827,217 B2 | 11/2017 | Martinez et al. |
| 9,884,813 B1 | 2/2018 | Martinez et al. |
| 9,962,348 B2 | 5/2018 | Tavazoie et al. |
| 2002/0022018 A1 | 2/2002 | Curiel et al. |
| 2002/0107233 A1 | 8/2002 | Liao et al. |
| 2003/0022375 A1 | 1/2003 | Itoh et al. |
| 2003/0027335 A1 | 2/2003 | Ruley et al. |
| 2003/0125357 A1 | 7/2003 | Adams et al. |
| 2003/0153541 A1 | 8/2003 | Dudley et al. |
| 2004/0072868 A1 | 4/2004 | Collins et al. |
| 2004/0087632 A1 | 5/2004 | Van Camp et al. |
| 2004/0216178 A1 | 10/2004 | Jones et al. |
| 2005/0080111 A1 | 4/2005 | Bayne et al. |
| 2005/0107444 A1 | 5/2005 | Thompsom et al. |
| 2005/0113419 A1 | 5/2005 | Huang et al. |
| 2005/0113580 A1 | 5/2005 | Thompson et al. |
| 2005/0130919 A1 | 6/2005 | Xu et al. |
| 2005/0131014 A1 | 6/2005 | Collini et al. |
| 2005/0215577 A1 | 9/2005 | Dehmlow et al. |
| 2005/0245515 A1 | 11/2005 | Dehmlow et al. |
| 2005/0261319 A1 | 11/2005 | Deuschle et al. |
| 2005/0282908 A1 | 12/2005 | Collins et al. |
| 2005/0289659 A1 | 12/2005 | Jacks et al. |
| 2006/0030612 A1 | 2/2006 | Steffan et al. |
| 2006/0074115 A1 | 4/2006 | Dehmlow et al. |
| 2006/0135601 A1 | 6/2006 | Dehmlow et al. |
| 2006/0178398 A1 | 8/2006 | Adams et al. |
| 2007/0093524 A1 | 4/2007 | Nambi et al. |
| 2007/0161553 A1 | 7/2007 | Mathieu et al. |
| 2009/0004297 A1 | 1/2009 | Ranganathan |
| 2009/0030082 A1 | 1/2009 | Forman |
| 2009/0099066 A1 | 4/2009 | Moulton et al. |
| 2009/0175791 A1 | 7/2009 | Kavile et al. |
| 2009/0247587 A1 | 10/2009 | Okuda et al. |
| 2009/0286780 A1 | 11/2009 | Okuda et al. |
| 2010/0048944 A1 | 2/2010 | Parhami |
| 2010/0056481 A1 | 3/2010 | Glausch et al. |
| 2010/0069367 A1 | 3/2010 | Boren et al. |
| 2010/0273816 A1 | 10/2010 | Bernotas et al. |
| 2010/0279918 A1 | 11/2010 | Langel et al. |
| 2010/0284990 A1 | 11/2010 | Kaemmerer et al. |
| 2010/0298410 A1 | 11/2010 | Obad et al. |
| 2011/0028384 A1 | 2/2011 | Blacklow et al. |
| 2011/0112135 A1 | 5/2011 | Singhaus, Jr. et al. |
| 2011/0166079 A1 | 7/2011 | Vitek et al. |
| 2011/0237791 A1 | 9/2011 | Kawaguchi et al. |
| 2012/0156216 A1 | 6/2012 | Oh |
| 2012/0156263 A1 | 6/2012 | Choy et al. |
| 2013/0004481 A1 | 1/2013 | Solca et al. |
| 2013/0071403 A1 | 3/2013 | Rolland et al. |
| 2015/0023955 A1 | 1/2015 | Tavazoie et al. |
| 2015/0033693 A1 | 2/2015 | Ito et al. |
| 2015/0045399 A1 | 2/2015 | Mohan |
| 2015/0051214 A1 | 2/2015 | Dong et al. |
| 2015/0065515 A1 | 3/2015 | Dong et al. |
| 2015/0073053 A1 | 3/2015 | Tavazoie et al. |
| 2015/0080406 A1 | 3/2015 | Leftheris et al. |
| 2015/0152094 A1 | 6/2015 | Mohan |
| 2015/0225366 A1 | 8/2015 | Li |
| 2015/0246924 A1 | 9/2015 | Dong et al. |
| 2015/0299136 A1 | 10/2015 | Busch et al. |
| 2017/0066791 A1 | 3/2017 | Martinez et al. |
| 2017/0119807 A1 | 5/2017 | Lee et al. |

FOREIGN PATENT DOCUMENTS

| | | |
|---|---|---|
| AU | 2003226094 A1 | 10/2003 |
| AU | 2006227435 A1 | 9/2006 |
| AU | 2005272043 B2 | 7/2010 |
| CA | 2592367 C | 4/2011 |
| CN | 101952293 A | 1/2011 |
| DE | 2951400 A1 | 7/1981 |
| EP | 0015505 B1 | 8/1984 |
| EP | 0519596 A1 | 12/1992 |
| EP | 0592106 A1 | 4/1994 |
| EP | 0735144 B1 | 6/2002 |
| EP | 2235019 A1 | 10/2010 |
| EP | 2474617 A1 | 7/2012 |
| EP | 2188266 B1 | 10/2012 |
| ES | 2233700 T3 | 6/2005 |
| ES | 2525217 T3 | 12/2014 |
| ES | 2694726 T3 | 12/2018 |
| FR | 2865736 B1 | 7/2006 |
| GB | 946902 A | 1/1964 |
| JP | H11507371 A | 6/1999 |
| JP | 200333179 A | 2/2003 |
| JP | 2006-232703 A | 9/2006 |
| JP | 2008/526841 A | 7/2008 |
| JP | 2008/179562 A | 8/2008 |
| JP | 2011-525616 A | 9/2011 |
| JP | 5399262 B2 | 1/2014 |
| JP | 5511079 B2 | 6/2014 |
| JP | 5851400 B2 | 2/2016 |
| KR | 10-2007-0116060 A | 12/2007 |
| KR | 10-2010-0102110 A | 9/2010 |
| MX | 2010/012579 A | 12/2010 |
| RU | 2383524 C2 | 3/2010 |
| TW | 2006/06157 A | 2/2006 |
| TW | 2008/25054 A | 6/2008 |
| TW | 2009/22582 A | 6/2009 |
| WO | WO-96/39135 A1 | 12/1996 |
| WO | WO-00/66611 A1 | 11/2000 |
| WO | WO-01/66534 A2 | 9/2001 |
| WO | WO-02/13594 A1 | 2/2002 |
| WO | WO-02/24632 A2 | 3/2002 |
| WO | WO-02/090375 A2 | 11/2002 |
| WO | WO-03/031408 A2 | 4/2003 |
| WO | WO-03/043998 A1 | 5/2003 |
| WO | WO-03/045382 A1 | 6/2003 |
| WO | WO-03/059874 A2 | 7/2003 |
| WO | WO-03/059884 A1 | 7/2003 |
| WO | WO-03/060078 A2 | 7/2003 |
| WO | WO-03/082205 A2 | 10/2003 |
| WO | WO-03/082802 A1 | 10/2003 |
| WO | WO-2003/082198 A2 | 10/2003 |
| WO | WO-03/090732 A1 | 11/2003 |
| WO | WO-03/090746 A1 | 11/2003 |
| WO | WO-03/090869 A1 | 11/2003 |
| WO | WO-03/099769 A1 | 12/2003 |
| WO | WO-03/099775 A1 | 12/2003 |
| WO | WO-03/106435 A1 | 12/2003 |
| WO | WO-2004/009091 A1 | 1/2004 |
| WO | WO-2004/011448 A1 | 2/2004 |
| WO | WO-2004/026816 A1 | 4/2004 |
| WO | WO-2004/043939 A1 | 5/2004 |
| WO | WO-2004/058717 A1 | 7/2004 |
| WO | WO-2004/072041 A1 | 8/2004 |
| WO | WO-2004/072042 A2 | 8/2004 |
| WO | WO-2004/072046 A1 | 8/2004 |
| WO | WO-2004/078939 A2 | 9/2004 |
| WO | WO-2005/005416 A1 | 1/2005 |
| WO | WO-2005/005417 A1 | 1/2005 |
| WO | WO-2005/016277 A2 | 2/2005 |
| WO | WO-2005/023782 A1 | 3/2005 |
| WO | WO-2005/039643 A2 | 5/2005 |
| WO | WO-2005/058834 A2 | 6/2005 |
| WO | WO-2005/077122 A2 | 8/2005 |
| WO | WO-2005/077124 A2 | 8/2005 |
| WO | WO-2005/112620 A2 | 12/2005 |
| WO | WO-2005/113499 A1 | 12/2005 |
| WO | WO-2006/000323 A1 | 1/2006 |
| WO | WO-2006/003923 A1 | 1/2006 |
| WO | WO-2006/017055 A2 | 2/2006 |
| WO | WO-2006/046593 A1 | 5/2006 |
| WO | WO-2006/073363 A1 | 7/2006 |
| WO | WO-2006/073364 A1 | 7/2006 |
| WO | WO-2006/073365 A1 | 7/2006 |
| WO | WO-2006/073366 A1 | 7/2006 |
| WO | WO-2006/073367 A1 | 7/2006 |
| WO | WO-2006/094034 A1 | 9/2006 |
| WO | WO-2006/102067 A1 | 9/2006 |

(56) References Cited

FOREIGN PATENT DOCUMENTS

| | | |
|---|---|---|
| WO | WO-2006/109633 A1 | 10/2006 |
| WO | WO-2007/002563 A1 | 1/2007 |
| WO | WO-2007/022563 A1 | 3/2007 |
| WO | WO-2007/047991 A1 | 4/2007 |
| WO | WO-2007/050425 A2 | 5/2007 |
| WO | WO-2007/081335 A1 | 7/2007 |
| WO | WO-2007/092065 A2 | 8/2007 |
| WO | WO-2008/011071 A2 | 1/2008 |
| WO | WO-2008/027988 A2 | 3/2008 |
| WO | WO-2008/049047 A2 | 4/2008 |
| WO | WO-2008/065754 A1 | 6/2008 |
| WO | WO-2009/020683 A2 | 2/2009 |
| WO | WO-2009/021868 A2 | 2/2009 |
| WO | WO-2009/024550 A1 | 2/2009 |
| WO | WO-2009/040289 A2 | 4/2009 |
| WO | WO-2009/043353 A2 | 4/2009 |
| WO | WO-2009/074467 A1 | 6/2009 |
| WO | WO-2009/086123 A1 | 7/2009 |
| WO | WO-2009/086129 A1 | 7/2009 |
| WO | WO-2009/086130 A1 | 7/2009 |
| WO | WO-2009/086138 A1 | 7/2009 |
| WO | WO-2009/133692 A1 | 11/2009 |
| WO | WO-2009/138438 A1 | 11/2009 |
| WO | WO-2009/144961 A1 | 12/2009 |
| WO | WO-2009/148915 A2 | 12/2009 |
| WO | WO-2009/150109 A1 | 12/2009 |
| WO | WO-2010/023317 A1 | 3/2010 |
| WO | WO-2010/025169 A2 | 3/2010 |
| WO | WO-2010/025179 A1 | 3/2010 |
| WO | WO-2010/036613 A1 | 4/2010 |
| WO | WO-2010/059627 A1 | 5/2010 |
| WO | WO-2010/125811 A1 | 11/2010 |
| WO | WO-2010/138598 A2 | 12/2010 |
| WO | WO-2011/014661 A2 | 2/2011 |
| WO | WO-2011/051282 A1 | 5/2011 |
| WO | WO-2011/055391 A1 | 5/2011 |
| WO | WO-2011/103175 A2 | 8/2011 |
| WO | WO-2011/115892 A1 | 9/2011 |
| WO | WO-2011/130426 A2 | 10/2011 |
| WO | WO-2011/158667 A1 | 12/2011 |
| WO | WO-2012/004748 A1 | 1/2012 |
| WO | WO-2012/095505 A1 | 7/2012 |
| WO | WO-2012/096573 A1 | 7/2012 |
| WO | WO-2012/135082 A1 | 10/2012 |
| WO | WO-2013/043569 A1 | 3/2013 |
| WO | WO-2013/057148 A1 | 4/2013 |
| WO | WO-2013/076257 A1 | 5/2013 |
| WO | WO-2013/130892 A1 | 9/2013 |
| WO | WO-2013/138565 A1 | 9/2013 |
| WO | WO-2013/138568 A1 | 9/2013 |
| WO | WO-2014/028461 A2 | 2/2014 |
| WO | WO-2014/144037 A1 | 9/2014 |
| WO | WO-2015/106164 A1 | 7/2015 |
| WO | WO-2018/161054 A1 | 9/2018 |

OTHER PUBLICATIONS

Ju et al. Oncology Letters 14, 7676-7680 (2017) (Year: 2017).*
Rough et al. Journal of Ovarian Research 3(13) (2010) (Year: 2010).*
Bobin-Dubigeon et al. in Anticancer Research 37(10), 5495-5498 (2017) (Year: 2017).*
Chuu et al. in Anticancer Research 30, 3643-3648 (2010) (Year: 2010).*
Bartel et al., "MicroRNAs: Target Recognition and Regulatory Functions," Cell. 136(2): 215-233 (2009).
Berge et al., "Pharmaceutical salts," J Pharm Sci. 66(1):1-1.
Bergenfelz et al., "Systemic Monocytic-MDSCs Are Generated from Monocytes and Correlate with Disease Progression in Breast Cancer Patients," PLOS One. 10(5):1-23 (2015).
Bird et al.,"Single-chain antigen-binding proteins," Science. 242(4877): 423-426 (1988).
Brunton et al., "Goodman and Gilman's The Pharmacological Basic of Therapeutics," McGraw Hill Companies (2011).
Bustin et al., "Absolute quantification of mRNA using real-time reverse transcription polymerase chain reaction assays," Journal of Molecular Endocrinology. 25(2): 169-193 (2000).
Calin et al., "MicroRNA signatures in human cancers," Nat Rev Cancer. 6: 857-866 (2007).
Caplus AN 1981:121135 for Ostermayer et al., "3-Amino-1, 2-propane diol derivates and pharmaceutical compositions containing them," (1981) (2 pages).
Caplus AN 1981:586827 for Mohr, R., "N, N'—Diarylethylendiamines or N, N', N"—triaryldiethylenetriamines," (1981) (1 page).
Caplus AN 1983:178855 for Fujikura et al., "Studies on benzenesulfonamide derivates with α- and β-adrenergic antagonistic and antihypertensive activities," Chemical & Pharmaceutical Bulletin 30(11):4092-101 (1982).
Caplus AN 2002:240713 for Collins et al., "Preparation of substituted phenylacetamides and benzamides as agonists for Liver X receptors (LXR)," (2002) (2 pages).
Caplus AN 2003:796421 for Cairns et al., "Methods of treatment with LXR modulators," (2003).
Caplus AN 2003:796645 for Thompson et al., "Preparation of (hetero)arylalkanoic acids and esters as LXR agonists," (2003) (2 pages).
Caplus, AN 2005:238962, for Yamazaki et al., "Preparation of azole compounds as PPAR-alpha agonists," (2005) (4 pages).
Caplus, AN 2006:910678, for Yamaguchi et al., "Preparation of phenoxyacetic acid compounds containing furan moiety as peroxisome proliferator activation receptor (PPAR) alpha/gamma agonists," (2006) (2 pages).
Carell et al., "A Solution-Phase Screening Procedure for the Isolation of Active Compounds from a Library of Molecules," Angewandte Chemie International Edition in English. 33(20): 2061-2064 (1994).
Cho et al., "An unnatural biopolymer," Science. 261 (5126): 1303-1305 (1993).
Chuu et al., "Modulation of liver X receptor signaling as novel therapy for prostate cancer," J Biomed Sci. 14(5):543-553 (2007).
Communication pursuant to Article 94(3) EPC for European Application No. 15734952.3, dated Jul. 18, 2019 (6 pages).
Communication pursuant to Article 94(3) EPC for European Patent Application No. 15734952.3, dated Aug. 29, 2018 (6 pages).
Cristiano et al., "Molecular conjugates: a targeted gene delivery vector for molecular medicine," J Mol Med. 73:479-486 (1995).
Cull et al., "Screening for receptor ligands using large libraries of peptides linked to the C terminus of the lac repressor," Proc Natl Acad Sci. 89(5): 1865-1869. (1992).
Cwirla et al., "Peptides on phage: A vast library of peptides for identifying ligands,"Proc Nati Acad Sci. 87: 6378-6382(1990).
Devlin et al., "Random peptide libraries: a source of specific protein binding molecules," Science. 249(4967): 404-406 (1990).
Dewitt et al., ""Diversomers": an approach to nonpeptide, nonoligomeric chemical diversity," Proc Natl Acad Sci. 90(15): 6909-6913 (1993).
Erb et al., "Recursive deconvolution of combinatorial chemical libraries," Proc Natl Acad Sci. 91(24), 11422-11426 (1994).
Examination Report for European Application No. 13829165.3, dated Jan. 15, 2018 (5 pages).
Examination Report No. 1 for Australian Patent Application No. 2013302861, dated Sep. 8, 2017 (6 pages).
Extended European Search Report for European Application No. 13829165.3, dated Jun. 8, 2016 (12 pages).
Extended European Search Report for European Patent Application No. 15734952.3, dated Jul. 6, 2017 (8 pages).
Fabian et al., "Regulation of mRNA Translation and Stability by microRNAs," Annu Rev Biochem. 79:351-379 (2010).
Felici et al., "Selection of Antibody Ligands from a Large Libraryof Oligopeptides Experessed on a Multivalent Exposition Vector," J. Mol. Biol. 222: 301-310 (1991).
Filipowicz et al., "Mechanisms of post-transcriptional regulation by MicroRNAs: are the answers in sight?," Nat Rev Genet. 9: 102-114 (2008).
First Examination Report for Australian Application No. 2015204572, dated Jul. 15, 2019 (7 pages).
First Office Action and Search Report for Chinese Application No. 2013800534784, dated Aug. 1, 2017 (19 pages).

(56) References Cited

OTHER PUBLICATIONS

Fodor et al., "Multiplexed biochemical assays with biological chips," Nature. 364: 555-556 (1993).
Fowler et al., "Liver X receptor activators display anti-inflan contact dermatitis models: liver-X-receptor-specific inhibitic production," J Invest Dermatol. 120(2):246-55 (2003).
Gallop et al., "Applications of Combinatorial Technologies to Drug Discovery. 1. Background and Peptide Combinatorial Libraries," J. Med Chem. 17:1233 (1994).
Garbe et al., "Melanoma epidemiology and trends," Clinics in Dermatology. 27(1): 3-9. (2009).
Garbe et al., "Systematic review of medical treatment in melanoma: current status and future prospects," Oncologist. 16(1):5-24 (2011).
Garzon et al., "Targeting microRNAs in cancer: rationale, strategies and challenges," Nat Rev Drug Discov. 9: 775-789 (2010).
Gielen et al., "Increase In Both CD14-Positive and CD15-Positive Myeloid-Derived Suppresor Cell Subpopulations in the Blood of Patients With Glioma But Predominance of CD15-Positive Myeloid-Derived Suppresor Cells in Glioma Tissue," J Neuropathol Exp Neur. 74(5):390-400 (2015).
Ginzinger et al., "Gene quantification using real-time quantitative PCR," Exp Hematol. 30(6): 503-512(2002).
Gros et al., "Myeloid Cells Obtained from the Blood but Not from the Tumor can Suppress T-cell Proliferation in Patients with Melanoma," Clin Cancer Res. 18(19):5212-5223 (2012).
Guo et al., "Mammalian microRNAs predominantly act to decrease target mRNA levels," Nature. 466:835-840 (2010).
Gupta et al., "Cancer Metastasis: Building a Framework," Cell. 127(4): 679-695 (2006).
Gupta et al., "Long non-coding RNA HOTAIR reprograms chromatin state to promote cancer metastasis," Nature. 464:1071-1076 (2010).
Guttman et al., "Chromatin signature reveals over a thousand highly conserved large non-coding RNAs in mammals," Nature. 458: 223-227 (2009).
Haas, Michael J., "Melanoma: three ways around BRAF inhibition," SciBX. 3(47):(2010) (3 pages).
Hanahan et al., "Hallmarks of Cancer: The Next Generation," Cell. 144(5): 646-674 (2011).
Haqq et al., "The gene expression signatures of melanoma progression," Proc. Natl. Acad. Sci. USA. 102(17): 6092-6097 (2005).
Hatters et al., "Apolipoprotein E structure: insights into function," Trends in Biochemical Sciences. 31(8): 445-454 (2006).
Hatziapostolou et al., "An HNF4a-miRNA Inflammatory Feedback Circuit Regulates Hepatocellular Oncogenesis," Cell. 147): (6)1233-1247 (2011).
Hauser et al., "Apolipoprotein E: From lipid transport to neurobiology," Progress in Lipid Research. 50(1): 62-74 (2001).
Huang et al., "The microRNAs miR-373 and miR-520c promote tumour invasion and metastasis," Nat Cell Biol. 10(2): 202-210 (2008).
Huarte et al., "A Large Intergenic Noncoding RNA Induced by p53 Mediates Global Gene Repression in the p53 Response," Cell. 142(3): 409-419 (2010).
Hurst et al., "Metastamir: The Field of Metastasis-Regulatory microRNA Is Spreading," Cancer Res. 69(19): 7495-7498 (2009).
Huston et al., "Protein engineering of antibody binding sites: recovery of specific activity in an anti-digoxin single-chain Fv analogue produced in *Escherichia coli.*," Proceedings of the National Academy of Sciences. 85(16): 5879-5883 (1988).
Hynes et al., "Metastatic Potential: generic predisposition of the primary tumor or rare, metastatic variants-or both?," Cell. 113(7): 821-823 (2003).
Iclozan et al.,"Therapeutic regulation of myeloid-derived suppressor cells and immune response to cancer vaccine in patients with extensive stage small cell lung cancer," Cancer Immunol Immunother. 62(5): 909-918 (2013).
International Preliminary Report on Patentability for International Patent Application No. PCT/US15/66289, dated Jun. 29, 2017 (7 pages).
International Preliminary Report on Patentability for International Patent Application No. PCT/US2015/010909, dated Jul. 21, 2016 (7 pages).
International Search Report and Written Opinion for International Application No. PCT/US15/66289, dated Feb. 25, 2016 (14 pages).
International Search Report and Written Opinion for International Application No. PCT/US18/62063, dated Feb. 4, 2019 (20 pages).
International Search Report and Written Opinion for International Patent Application No. PCT/US2015/010909, dated Jun. 11, 2015 (14 pages).
Invitation to Pay Additional Fees for International Applicatication No. PCT/US2015/010909, mailed Mar. 11, 2015 (3 pages).
Jemal et al., "Cancer Statistics, 2008," CA Cancer J Clin. 58(2): 71-96. (2008).
Kang et al., "A multigenic program mediating breast cancer metastasis to bone," Cancer Cell, 3(6): 537-549 (2003).
Kitano et al. "Computational algorithm-driven evaluation of monocytic myeloid-derived suppressor cell frequency for prediction of clinical outcomes," Cancer Immunol Res. 2(8): 812-821 (2014).
Lam et al., "A new type of synthetic peptide library for identifying ligand-binding activity," Nature. 354(6348): 82-84 (1991).
Li et al., "Liver X receptor modulators: a review of recently patented compounds (2007-2009)," Expert Opin Ther Pat. 20(4):535-62 (2010).
Li et al., "miR-495 and miR-551 a inhibit the migration and invasion of human gastric cancer cells by directly interacting with PRL-3," Cancer Lett. 323(1):41-47 (2012).
Loewer et al. "Large intergenic non-coding RNA-RoR modulates reprogramming of human induced pluripotent stem cells," Nat Genet. 42(12): 1113-1117 (2010).
Lucas et al. "Solar ultraviolet radiation: Global burden of disease from solar ultraviolet radiation," Environmental Burden of Disease Series, 13 (2006) (95 pages).
Lujambio et al., "The microcosmos of cancer," Nature. 482(7385): 347-355 (2012).
Ma et al., "Tumour invasion and metastasis initiated by microRNA-10b in breast cancer," Nature. 449(7163): 682-688 (2007).
Marino et al., "The discovery of tertiary-amine LXR agonist with potent cholesterol efflux activity in macrophages," Bioorg Med Chem Lett. 19(19):5617-21 (2009).
Minn et al., "Genes that mediate breast cancer metastasis to lung," Nature. 436(7050): 518-524 (2005).
Obermajer et al., "PGE$_2$-Induced CXCL12 Production and CXCR4 Expression Controls the Accumulation of Human MDSCs in Ovarian Cancer Environment," Cancer Res 71(24): 7463-7470 (2011) (9 pages).
Office Action for Japanese Application No. 2015-527533, dated Jun. 6, 2017 (13 pages).
Office Action for Japanese Application No. 2015-527533, dated Nov. 14, 2017 (5 pages).
Olson et al., "MIcroRNA dynamics In the stages of tumorigenesis correlate with hallmark capabilities of cancer," Genes Dev. 23(18): 2152-2165 (2009).
Ong et al., "Quantitative Real-time PCR: A Critique of Method and Practical Considerations," Hematology. 7(1): 59-67 (2002).
Ostrand-Rosenberg et al., "Myeloid-derived suppressor cells: linking inflammation and cancer," J Immunol.182(8):4499-4506 (2009).
Padlan et al., "A possible procedure for reducing the immunogenicity of antibody variable domains while preserving their ligand-binding properties," Mol Immunol. 28(4-5): 489-498 (1991).
Pencheva et al. "Control of Metastatic Progression by microRNA Regulatory Networks," Available in PMC Dec. 15, 2015, published in final edited form as: Nat Cell Biol. 15(6):546-554 (2013) (21 pages).
Pencheva et al., "Broad-Spectrum therapeutic suppression of metastatic melanoma through nuclear hormone receptor activation," Cell 156(5):986-1001 (2014).
Pencheva et al., "Convergent multi-miRNA targeting of ApoE drives LRP1/LRP8-dependent melanoma metastasis and angiogenesis," available in PMC Nov. 21, 2013, published in final edited form as: Cell. 151 (5):1068-82 (2012) (27 pages).

(56) References Cited

OTHER PUBLICATIONS

Png et al., "A microRNA regulon that mediates endothelial recruitment and metastasis by cancer cells," Nature. 481(7380): 190-194 (2011).
Poliseno et al., "A coding-independent function of gene and pseudogene mRNAs regulates tumour biology," Nature. 465(7301): 1033-1038 (2010).
Pollack et al., "Use of Young Nude Mice for Selection of Subpopulations of Cells With Increased Metastatic Potential From Nonsyngeneic Neoplasms," J Natl Cancer Inst. 69(1): 137-141 (1982).
Ponomarev et al., "A novel triple-modality reporter gene for whole-body fluorescent, bioluminescent, and nuclear noninvasive imaging," Eur J Nucl Med Mol Imaging. 31(5): 740-751 (2004).
PubChem Compound Summary for CID 10301050, Created Oct. 25, 2006, Modified Jan. 19, 2019 (9 pages).
PubChem Compound Summary for CID 422253, Created Mar. 26, 2005, Modified Jan. 19, 2019 (11 pages).
PubChem Substance Record for SID 168474198, available Dec. 2, 2013 (6 pages).
PubChem. Compound Summary for CID 51369, created Mar. 27, 2005, <https://pubchem.ncbi.nlm.nih.gov/compound/51369?from=summary>, retrieved on Feb. 23, 2015 (18 pages).
PubChem. Compound Summary for CID 52723103, created May 20, 2011 <https://pubchem.ncbi.nlm.nih.gov/compound/52723103>, retrieved on Nov. 7, 2016 (3 pages).
Riddell et al. "The LXR agonist TO901317 selectively lowers hippocampal Abeta42 and improves memory in the Tg2576 mouse model of Alzheimer's disease," Mol Cell Neurosci. 34(4):621-8 (2007).
Riechmann et al., "Reshaping human antibodies for therapy," Nature. 332(6162): 323-327 (1988).
Roguska et al., "Humanization of murine monoclonal antibodies through variable domain resurfacing," Proceedings of the National Academy of Sciences. 91(3): 969-973 (1994).
Roz et al., "Macrophage apolipoprotein E and proliferation of MCF-7 breast cancer cells: role of LXR," Anticancer Res. 33(9):3783-9 (2013).
Rudolph et al. "Increased frequencies of CD11b+CD33+CD14+HLA-DRlow myeloid-derived suppressor cells are an early event in melanoma patients," Exp Dermatology 23(3):202-204 (2014).
Schmuth et al. "Thematic review series: skin lipids. Peroxisome proliferator-activated receptors and liver X receptors in epidermal biology," J Lipid Res. 49(3):499-509 (2008).
Scoles et al. "Liver X receptor agonist inhibits proliferation of ovarian carcinoma cells stimulated by oxidized low density lipoprotein," Gynecol Oncol. 116(1):109-116 (2010).
Scott et al., "Searching for peptide ligands with an epitope library," Science. 249(4967): 386-390 (1990).
Second Office Action tor Chinese Application No. 2013800534784, dated Mar. 13, 2018 (8 pages).
Spencer et al., "Pharmacophore Analysis of the Nuclear Oxysterol Receptor LXRa," J Med Chem. 44(6), 886-897 (2001).
Studnicka et al., "Human-engineered monoclonal antibodies retain full specific binding activity by preserving non-CDR complementarity-modulating residues," Protein Engineering, Design and Selection. 7(6): 805-814 (1994).
Talmadge et al. "History of myeloid derived suppressor cells (MDSCs) in the macro- and micro-environment of tumour-bearing hosts," Available in PMC Mar. 13, 2015, published in final edited tor as: Nat Rev Cancer. 13(10):739-752 (2013) (34 pages).
Tavazoie et al., "Endogenous human microRNAs that suppress breast cancer metastasis," Nature. 451(7175): 147-152 (2008).
Thaker et al., "In Situ RT-PCR and Hybridization Techniques," Methods Mol Biol. 115: 379-402 (1999).
Viennois et al. "Selective liver X receptor modulators (SLIMs): What use in human health?" Mol Cell Endocrinol. 351(2):129-41 (2011).
Wang et al., "Gene-expression profiles to predict distant metastasis of lymph-node-negative primary breast cancer," Lancet. 365(9460): 671-679 (2005).
Ward et al. "Binding activities of a repertoire of single immunoglobulin variable domains secreted from *Escherichia coli*," Nature. 341(6242): 544-546 (1989).
Weber et al. "Phase I/II Study of Metastatic Melanoma Patients Treated with Nivolumab Who Had Progressed after Ipilimumab," Cancer Immunol Res 4(4):345-53 (2016) (10 pages).
Zhang et al. "A novel subset of B7-H3$^+$CD14$^+$HLA-DR$^{-/low}$ myeloid-derived suppressor cells are associated with progression of human NSCLC," *OncoImmunology* 4(2): e977164-1-12 (2015).
Zhang et al. "Liver X receptor activation induces apoptosis of melanoma cell through caspase pathway," Cancer Cell Int. 14(1):1-6 (2014).
Zhang et al., "The microRNA network and tumor metastasis," Oncogene. 29(7): 937-948 (2010).
Zigler et al."Tumor Immunotherapy in Melanoma: Strategic for Overcoming Mechanisms of Resistance and Escape," Am J Clin Dermatol. 9(5):307-313 (2008).
Zuckermann et al., "Discovery of Nanomolar Ligands for 7-Transmembrane G-Protein-Coupled Receptors from a Diverse N-(Substituted)glycine Peptoid Library," J Med Chem. 37(17): 2678-2685 (1994).
Adeyeye et al., "Diclofenac sodium," Analytical Profiles of Drug Substances. 19:123-44 (1990) (23 pages).
Bastin et al., "Salt selection and optimisation procedures for pharmaceutical new chemical entities," Org. Process Res. Dev. 4(5):427-35 (2000).
International Search Report and Written Opinion for International Application No. PCT/US20/64456, dated Mar. 3, 2021 (13 pages).

\* cited by examiner

| RT (min) | PeakName | Area (mAU*s) | Area % | Amount (mg/mL) | Peak Type |
|---|---|---|---|---|---|
| 7.66 | RGX-104 | 4215.254 | 99.583 | 0.0000 | BV |
| 7.89 | | 4.843 | 0.114 | 0.0000 | VB |
| 8.30 | | 2.165 | 0.051 | 0.0000 | BV |
| 8.97 | | 1.224 | 0.029 | 0.0000 | BB |
| 9.40 | RGX-108 | 9.434 | 0.223 | 0.0000 | BB |

POLYMORPHS AND USES THEREOF

BACKGROUND

The Liver X Receptor (LXR) is a nuclear receptor transcription factor. It has been found that LXR modulators are useful in the treatment of a variety of diseases, including cancers. There is a need to provide crystalline forms of such compounds with improved physical properties.

SUMMARY OF THE INVENTION

The invention provides a crystalline ansolvate of an LXRβ agonist and several crystalline solvates of the LXRβ agonist. The invention also provides a method of preparing the crystalline forms of the LXRβ agonist, pharmaceutical compositions comprising the LXRβ agonist, and a method of treating cancer with such compositions.

Accordingly, in an aspect, the invention features a crystalline ansolvate of the hydrochloride salt of compound 1 having the structure:

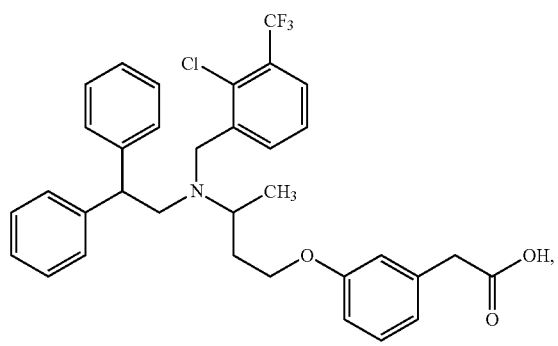 [SMILES: CC(CCOc1cccc(CC(=O)O)c1)N(Cc1cccc(C(F)(F)F)c1Cl)CC(c1ccccc1)c1ccccc1]

1 wherein the crystalline ansolvate has at least one peak at diffraction angle 2θ (°) of 9.7°±0.5, 11.4°±0.5, 15.0°±0.5, 17.3°±0.5, 18.8°±0.5, and/or 19.3°±0.5 as measured by X-ray diffractometry or calculated from X-ray diffractometry.

In some embodiments, the crystalline ansolvate has one or more (e.g., two or more, three or more, four or more, five or more, six or more, seven or more, eight or more, nine or more, ten or more, eleven or more, twelve or more, thirteen or more, fourteen or more) peaks listed in Table 1 as measured by X-ray powder diffractometry. In some embodiments, the crystalline ansolvate has all of the peaks listed in Table 1 as measured by X-ray powder diffractometry.

TABLE 1

XRPD peak list for the crystalline ansolvate

| 2θ (°) | Intensity |
|---|---|
| 6.2044 | 16.18 |
| 8.5728 | 23.01 |
| 9.2398 | 1.65 |
| 9.7295 | 54.14 |
| 11.3847 | 62.72 |
| 12.1552 | 27.86 |
| 12.4279 | 32.17 |
| 12.5373 | 21.81 |
| 14.2819 | 17.87 |
| 14.6053 | 44.1 |
| 14.9936 | 100 |

TABLE 1-continued

XRPD peak list for the crystalline ansolvate

| 2θ (°) | Intensity |
|---|---|
| 16.2208 | 29.36 |
| 17.2919 | 85.01 |
| 17.382 | 64.09 |
| 17.8533 | 27.54 |
| 18.7703 | 80.99 |
| 19.0985 | 22.79 |
| 19.3406 | 85.25 |
| 19.579 | 46.38 |
| 20.1494 | 44.15 |
| 20.7655 | 5.72 |
| 21.5261 | 43.13 |
| 22.1189 | 39.07 |
| 22.868 | 41.04 |
| 23.1155 | 10.44 |
| 23.4014 | 17.53 |
| 24.0402 | 31.66 |
| 24.5102 | 23.98 |
| 24.7387 | 10.02 |
| 25.1939 | 33.67 |
| 25.65 | 23.73 |
| 25.8334 | 36.55 |
| 26.3363 | 6.03 |
| 27.4999 | 8.09 |
| 27.6386 | 10.22 |
| 27.8953 | 9.89 |
| 28.4944 | 17.53 |
| 28.8392 | 13.21 |
| 29.4733 | 16.3 |
| 30.2443 | 6.67 |
| 30.4481 | 8.84 |
| 31.3937 | 3.32 |
| 32.5168 | 11.61 |
| 32.8337 | 14.2 |
| 33.2407 | 8.54 |
| 33.5213 | 6.74 |
| 34.3935 | 8.31 |

In some embodiments, the crystalline ansolvate is substantially free of a solvated polymorph of compound 1. In some embodiments, the crystalline ansolvate has a loss of weight from 25° C. to 140° C. of less than 1% as measured by thermal gravimetric analysis. In some embodiments, the crystalline ansolvate has an endothermic onset at about 90° C. in differential scanning calorimetry (DSC) profile.

In another aspect, the invention features a crystalline solvate of the hydrochloride salt of compound 1 having the structure:

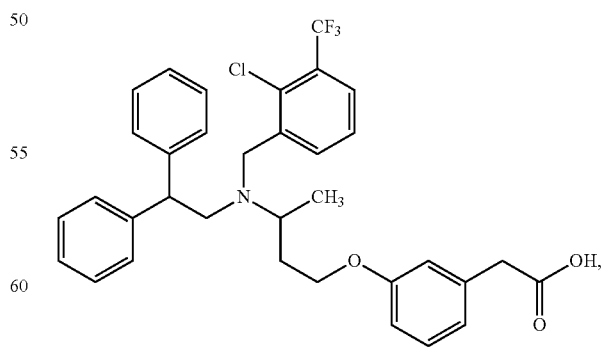

1 wherein the crystalline solvate has:
(i) at least one peak at diffraction angle 2θ (°) of 9.6±0.5, 15.9±0.5, 16.8±0.5, 18.1±0.5, 18.2±0.5, 18.8±0.5, 19.3±0.5, and/or 20.1±0.5 as measured by X-ray diffractometry or calculated from X-ray diffractometry;

(ii) at least one peak at diffraction angle 2θ (°) of 16.4±0.5 and/or 18.4±0.5 as measured by X-ray diffractometry or calculated from X-ray diffractometry;

(iii) at least one peak at diffraction angle 2θ (°) of 14.0±0.5, 18.5±0.5, and/or 21.3±0.5 as measured by X-ray diffractometry or calculated from X-ray diffractometry;

(iv) at least one peak at diffraction angle 2θ (°) of 9.6±0.5, 12.2±0.5, 15.9±0.5, 16.8±0.5, 18.0±0.5, and/or 20.4±0.5 as measured by X-ray diffractometry or calculated from X-ray diffractometry;

(v) at least one peak at diffraction angle 2θ (°) of 9.6±0.5, 12.10.5, 15.0±0.5, 18.4±0.5, 20.4±0.5, and/or 20.5±0.5 as measured by X-ray diffractometry or calculated from X-ray diffractometry;

(vi) at least one peak at diffraction angle 2θ (°) of 16.9±0.5 as measured by X-ray diffractometry or calculated from X-ray diffractometry;

(vii) at least one peak at diffraction angle 2θ (°) of 17.9±0.5 and/or 20.3±0.5 as measured by X-ray diffractometry or calculated from X-ray diffractometry; or (viii) at least one peak at diffraction angle 2θ (°) of 5.0±0.5, 13.9±0.5, 16.4±0.5, and/or 19.1±0.5 as measured by X-ray diffractometry or calculated from X-ray diffractometry.

In another aspect, the invention features a method of producing a crystalline ansolvate of the hydrochloride salt of compound 1 having the structure:

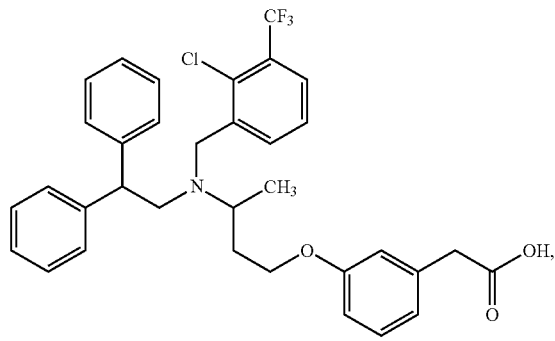

the method comprising:

(a) mixing amorphous compound 1 in tetrahydrofuran and an antisolvent (e.g., diisopropy ether), then cooling the mixture under conditions sufficient to form a first crystalline solvate of the compound;

(b) mixing the first crystalline solvate in toluene and cooling the slurry under conditions sufficient to form a second crystalline solvate of the compound;

(c) drying the second crystalline solvate under vacuum under conditions sufficient to produce a crystalline ansolvate of the compound, thereby producing a crystalline ansolvate of the compound.

In some embodiments, mixing amorphous compound 1 in tetrahydrofuran and an antisolvent of step (a) includes dissolving amorphous compound 1 in tetrahydrofuran and adding the antisolvent. In some embodiments of the method, step (a) includes cooling the mixture of amorphous compound 1 in tetrahydrofuran and antisolvent (e.g., diisopropyl ether) below 10° C. In some embodiments of the method, step (b) includes cooling the slurry of the first crystalline solvate in toluene below 10° C. In some embodiments of the method, step (c) comprises heating the second crystalline solvate under vacuum above 22° C.

In another aspect, the invention features a crystalline ansolvate produced by any of the foregoing methods.

In another aspect, the invention features a method of producing a pharmaceutical composition including compound 1 having the structure:

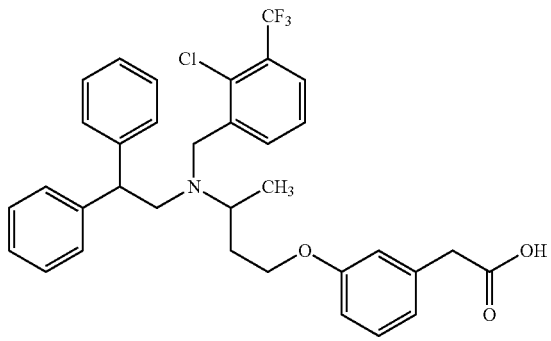

This method includes mixing a lipophilic vehicle, including a lipid excipient and/or a surfactant, and any of the foregoing crystalline ansolvates.

In some embodiments, the method includes dissolving the crystalline ansolvate in the lipophilic vehicle. In some embodiments, the method further comprises adding a sodium salt of a fatty acid. In some embodiments, the sodium salt of a fatty acid is added to the lipophilic vehicle before the crystalline ansolvate. In some embodiments, sodium chloride precipitates upon addition of the sodium salt of a fatty acid.

In some embodiments, the lipophilic vehicle comprises at least one glycerol linoleate. In some embodiments, the lipophilic vehicle comprises at least one lauroyl macrogol-32 glyceride. In some embodiments, the stabilizing agent comprises EDTA and/or sodium citrate. In some embodiments, the fatty acid carboxylate is a long chain fatty acid carboxylate, e.g., a saturated fatty acid carboxyate selected from caprylate, caprate, laurate, and/or stearate or an unsaturated fatty acid carboxyate selected from myristoelate, palmitoleate, sapienate, oleate, elaidate, and/or vaccenate. In some embodiments, the fatty acid carboxylate is oleate.

In another aspect, the invention features a method of treating cancer, the method comprising administering an effective amount of any of the foregoing pharmaceutical compositions.

In one embodiment of any of the foregoing methods, the subject has a cancer that has failed to respond to a previously administered immunotherapy (e.g., the cancer of the subject has progressed despite treatment with the immunotherapy).

In some embodiments of any of the foregoing methods, the cancer is resistant to an immunotherapy (e.g., the cancer has been determined to be resistant to immunotherapies such as by genetic markers or the level of MDSCs (e.g., monocytic and/or granulocytic MDSCs) in a sample, or is likely to be resistant, to immunotherapies such as a cancer that has failed to respond to an immunotherapy).

In another aspect, the invention features a method of treating cancer that has failed to respond to an immunotherapy in a subject, the method including administering an effective amount of an LXRβ agonist to the subject in combination with an immunotherapy.

In another aspect, the invention features a method of treating cancer that is resistant to immunotherapy in a subject, the method including administering an effective amount of an LXRβ agonist to the subject in combination with an immunotherapy.

In some embodiments, the cancer is breast cancer, colon cancer, renal cell cancer, non-small cell lung cancer, hepatocellular carcinoma, gastric cancer, ovarian cancer, pancreatic cancer, esophageal cancer, prostate cancer, sarcoma, glioblastoma, diffuse large B-cell lymphoma, leukemia, or melanoma. In some embodiments, the cancer is metastatic cancer.

In certain embodiments of any of the foregoing methods, the cancer is a drug resistant cancer or has failed to respond to a prior therapy (e.g., a cancer resistant to, or a cancer that has failed to respond to prior treatment with, vemurafenib, dacarbazine, a CTLA4 inhibitor, a PD1 inhibitor, interferon therapy, a BRAF inhibitor, a MEK inhibitor, radiotherapy, temozolimide, irinotecan, a CAR-T therapy, herceptin, perjeta, tamoxifen, xeloda, docetaxol, platinum agents such as carboplatin, taxanes such as paclitaxel and docetaxel, ALK inhibitors, MET inihibitors, alimta, abraxane, adriamycin, gemcitabine, avastin, halaven, neratinib, a PARP inhibitor, ARN810, an mTOR inhibitor, topotecan, gemzar, a VEGFR2 inhibitor, a folate receptor antagonist, demcizumab, fosbretabulin, or a PDL1 inhibitor).

In one embodiment of any of the foregoing methods, the immunotherapy, when present, is a CTLA-4 inhibitor, a PD1 inhibitor, a PDL1 inhibitor, or adoptive T-cell transfer therapy. In some embodiments, the immunotherapy is a PD-1 inhibitor such as a PD-1 antibody, a PD-L1 inhibitor such as a PD-L1 antibody, a CTLA-4 inhibitor such as a CTLA-4 antibody, a CSF-1R inhibitor, an IDO inhibitor, an A1 adenosine inhibitor, an A2A adenosine inhibitor, an A2B adenosine inhibitor, an A3A adenosine inhibitor, an arginase inhibitor, or an HDAC inhibitor. In some embodiments, the immunotherapy is a PD-1 inhibitor (e.g., nivolumab, pembrolizumab, pidilizumab, BMS 936559, and MPDL3280A). In some embodiments, the immunotherapy is a PD-L1 inhibitor (e.g., atezolizumab and MEDI4736). In some embodiments, the immunotherapy is a CTLA-4 inhibitor (e.g., ipilimumab). In some embodiments, the immunotherapy is a CSF-1R inhibitor (e.g., pexidartinib and AZD6495). In some embodiments, the immunotherapy is an IDO inhibitor (e.g., norharmane, rosmarinic acid, and alpha-methyl-tryptophan). In some embodiments, the immunotherapy is an A adenosine inhibitor (e.g., 8-cyclopentyl-1,3-dimethylxanthine, 8-cyclopentyl-1,3-dipropylxanthine, 8-phenyl-1,3-dipropyxanthine, bamifylline, BG-9719, BG-9928, FK-453, FK-838, rolofylline, or N-0861). In some embodiments, the immunotherapy is an A2A adenosine inhibitor (e.g., ATL-4444, istradefylline, MSX-3, preladenant, SCH-58261, SCH-412,348, SCH-442,416, ST-1535, VER-6623, VER-6947, VER-7835, viadenant, or ZM-241, 385). In some embodiments, the immunotherapy is an A2B adenosine inhibitor (e.g., ATL-801, CVT-6883, MRS-1706, MRS-1754, OSIP-339,391, PSB-603, PSB-0788, or PSB-1115). In some embodiments, the immunotherapy is an A3A adenosine inhibitor (e.g., KF-26777, MRS-545, MRS-1191, MRS-1220, MRS-1334, MRS-1523, MRS-3777, MRE-3005-F20, MRE-3008-F20, PSB-11, OT-7999, VUF-5574, and SSR161421). In some embodiments, the immunotherapy is an arginase inhibitor (e.g., an arginase antibody, (2s)-(+)-amino-5-iodoacetamidopentanoic acid, NG-hydroxy-L-arginine, (2S)-(+)-amino-6-iodoacetamidohexanoic acid, or (R)-2-amino-6-borono-2-(2-(piperidin-1-yl)ethyl)hexanoic acid. In some embodiments, the immunotherapy is an HDAC inhibitor (e.g., valproic acid, SAHA, or romidepsin).

In another embodiment of any of the foregoing methods, the method further includes administering to the subject an additional anticancer therapy (e.g., an antiproliferative).

In particular embodiments, the antiproliferative is: a chemotherapeutic or cytotoxic agent, a differentiation-inducing agent (e.g. retinoic acid, vitamin D, cytokines), a hormonal agent, an immunological agent, or an anti-angiogenic agent. Chemotherapeutic and cytotoxic agents include, but are not limited to, alkyating agents, cytotoxic antibiotics, antimetabolites, vinca alkaloids, etoposides, and others (e.g., paclitaxel, taxol, docetaxel, taxotere, cis-platinum). A list of additional compounds having antiproliferative activity can be found in L. Brunton, B. Chabner and B. Knollman (eds). Goodman and Gilman's The Pharmacological Basis of Therapeutics, Twelfth Edition, 2011, McGraw Hill Companies, New York, N.Y.

In certain embodiments, the antiproliferative is a PD1 inhibitor, a VEGF inhibitor, a VEGFR2 inhibitor, a PDL1 inhibitor, a BRAF inhibitor, a CTLA-4 inhibitor, a MEK inhibitor, an ERK inhibitor, vemurafenib, dacarbazine, trametinib, dabrafenib, MEDI-4736, an mTOR inhibitor, a CAR-T therapy, abiraterone, enzalutamide, ARN-509, 5-FU, FOLFOX, FOLFIRI, herceptin, xeloda, a PD1 antibody (e.g., pembrolizumab or nivolumab), a PDL-1 antibody, a CTLA-4 antibody (e.g, ipilimumab), ramucirumab, rindopepimut, glembatumumab, vedotin, ANG1005, and/or ANG4043.

In some embodiments, the cancer is a renal cell carcinoma and the antiproliferative is a PD1 inhibitor, a PDL-1 inhibitor, or an mTOR inhibitor. In other embodiments, the cancer is diffuse large B-cell lymphoma and the antiproliferative is a CAR-T therapy. In certain embodiments, the cancer is prostate cancer and the antiproliferative is abiraterone, enzalutamide, or ARN-509. In some embodiments, the cancer is hepatocellular carcinoma, gastric cancer, or esophageal cancer and the antiproliferative is 5-FU, FOLFOX, FOLFIRI, herceptin, or xeloda. In some embodiments, the cancer is sarcoma and the antiproliferative is gemcitabine. In other embodiments, the cancer is pancreatic cancer and the antiproliferative is irinotecan, cisplatin, abraxane, a taxane (e.g., paclitaxel or docetaxel), or capecitabine.

The method may further include administering an antiproliferative selected from the group consisting of alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists/antagonists, endothelin A receptor antagonist, retinoic acid receptor agonists, immuno-modulators, hormonal and antihormonal agents, photodynamic agents, tyrosine kinase inhibitors, antisense compounds, corticosteroids, HSP90 inhibitors, proteosome inhibitors (for example, NPI-0052), CD40 inhibitors, anti-CSI antibodies, FGFR3 inhibitors, VEGF inhibitors, MEK inhibitors, cyclin D1 inhibitors, NF-kB inhibitors, anthracyclines, histone deacetylases, kinesin inhibitors, phosphatase inhibitors, COX2 inhibitors, mTOR inhibitors, calcineurin antagonists, IMiDs, or other agents used to treat proliferative diseases.

In some embodiments of any of the foregoing methods, the cancer is breast cancer such as triple negative breast cancer, colon cancer, renal cell cancer, non-small cell lung cancer, hepatocellular carcinoma, gastric cancer, ovarian cancer, pancreatic cancer, esophageal cancer, prostate cancer, sarcoma, glioblastoma, diffuse large B-cell lymphoma, leukemia (e.g., acute myeloid leukemia), or melanoma. In some embodiments of any of the foregoing methods, the cancer is melanoma. In some embodiments of any of the foregoing methods, the cancer is breast cancer. In some embodiments of any of the foregoing methods, the cancer is renal cell cancer. In some embodiments of any of the foregoing methods, the cancer is pancreatic cancer. In some embodiments of any of the foregoing methods, the cancer is non-small cell lung cancer. In some embodiments of any of the foregoing methods, the cancer is colon cancer. In some embodiments of any of the foregoing methods, the cancer is ovarian cancer. In some embodiments of any of the foregoing methods, the cancer is glioblastoma. In some embodiments, the cancer is breast cancer. In some embodiments, the cancer is prostate cancer. In some embodiments, the cancer is diffuse large B-cell lymphoma. In some embodiments, the cancer is leukemia (e.g., acute myeloid leukemia).

In particular embodiments, the cancer is melanoma (e.g., metastatic melanoma) that is resistant to, or has failed to respond to prior treatment with, vemurafenib, dacarbazine, interferon therapy, a CTLA-4 inhibitor, a BRAF inhibitor, a MEK inhibitor, a PD1 inhibitor, a PDL-1 inhibitor, and/or a CAR-T therapy. In some embodiments, the cancer is glioblastoma that is resistant to, or has failed to respond to prior treatment with, temozolimide, radiotherapy, avastin, irinotecan, a VEGFR2 inhibitor, a CAR-T therapy, and/or an mTOR inhibitor. In some embodiments, the cancer is non-small cell lung cancer such as metastatic non-small cell lung cancer (e.g., EGFR-wild type non-small cell lung cancer and/or squamous non-small cell lung cancer) that is resistant to, or has failed to respond to prior treatment with, an EGFR inhibitor, platinum agents (e.g., carboplatin), avastin, an ALK inhibitor, a MET inhibitor, a taxane (e.g., paclitaxel and/or doceltaxel), gemzar, alimta, radiotherapy, a PD1 inhibitor, a PDL1 ihibitor, and/or a CAR-T therapy. In some embodiments, the cancer is a breast cancer (e.g., triple negative breast cancer) that is resistant to, or has failed to respond to prior treatment with, herceptin, perjeta, tamoxifen, xeloda, docetaxel, carboplatin, paclitaxel, abraxane, adriamycin, gemcitabine, avastin, halaven, neratinib, a PARP inhibitor, a PD1 inhibitor, a PDL1 inhibitor, a CAR-T therapy, ARN810, and/or an mTOR inhibitor. In some embodiments, the cancer is ovarian cancer (e.g., metastatic ovarian cancer) that is resistant to, or has failed to respond to prior treatment with, a PARP inhibitor, avastin, platinum agents such as carboplatin, paclitaxel, docetaxel, topotecan, gemzar, a VEGR2 inhibitor, a folate receptor antagonist, a PD1 inhibitor, a PDL1 inhibitor, a CAR-T therapy, demcizumab, and/or fosbretabulin.

Definitions

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

By "biological sample" or "sample" is meant a fluid or solid sample from a subject. Biological samples may include cells; nucleic acid, protein, or membrane extracts of cells; or blood or biological fluids including (e.g., plasma, serum, saliva, urine, bile). Solid biological samples include samples taken from feces, the rectum, central nervous system, bone, breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, and the thymus. Fluid biological samples include samples taken from the blood, serum, plasma, pancreatic fluid, CSF, semen, prostate fluid, seminal fluid, urine, saliva, sputum, mucus, bone marrow, lymph, and tears. Samples may be obtained by standard methods including, e.g., venous puncture and surgical biopsy. In certain embodiments, the biological sample is a blood, plasma, or serum sample. In some embodiments, the biological sample is a tumor sample from a biopsy.

The term "cancer" refers to any cancer caused by the proliferation of malignant neoplastic cells, such as tumors, neoplasms, carcinomas, sarcomas, leukemias, and lymphomas.

"Cell migration" as used in this application involves the invasion by the cancer cells into the surrounding tissue and the crossing of the vessel wall to exit the vasculature in distal organs of the cancer cell.

By "cell migration cancers" is meant cancers that migrate by invasion by the cancer cells into the surrounding tissue and the crossing of the vessel wall to exit the vasculature in distal organs of the cancer cell.

By "determining the level of a cell type" is meant the detection of a cell type by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third party laboratory that directly acquired the physical entity or value). Methods to measure cell levels generally include, but are not limited to, flow cytometry and immunohistochemistry. Exemplary methods are provided herein. In some embodiments of any of the foregoing methods, the level of MDSCs and/or activated T-cells may be determined as described in Iclozan et al. Cancer Immunol. Immunother. 2013, 62(5): 909-918. In some embodiments of any of the foregoing methods, the level of MDSCs and/or activated T-cells may be determined as described in Kitano et al. Cancer Immunol. Res. 2014, 2(8); 812-821.

A cancer "determined to be drug resistant," as used herein, refers to a cancer that is drug resistant, based on unresponsiveness or decreased responsiveness to a chemotherapeutic agent, or is predicted to be drug resistant based on a prognostic assay (e.g., a gene expression assay).

By a "drug resistant" cancer is meant a cancer that does not respond, or exhibits a decreased response to, one or more chemotherapeutic agents (e.g., any agent described herein).

The term "effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "effective amount" does not in fact require successful treatment be achieved in a particular individual. Rather, an effective amount may be that amount that provides a particular desired pharmacological response in a significant number of subjects when administered to patients in need of such treatment. It is specifically understood that particular subjects may, in fact, be "refractory" to an "effective amount." To give but one example, a refractory subject may have a low bioavailability such that clinical efficacy is not obtainable. In some embodiments, reference to an effective amount may be a reference to an amount as measured in one or more specific tissues (e.g., a tissue affected by the disease, disorder or condition) or fluids (e.g., blood, saliva, serum, sweat, tears, urine). Those of ordinary skill in the art will appreciate that, in some embodiments, an effective amount may be formulated and/or administered in a single dose. In some embodiments, an effective amount may be formulated and/or administered in a plurality of doses, for example, as part of a dosing regimen.

By "fatty acid" is meant a carboxylic acid with a long aliphatic chain either saturated or unsaturated. Short-chain fatty acids (SCFA) are fatty acids with aliphatic tails of fewer than six carbons (e.g. butyric acid). Medium-chain fatty acids (MCFA) are fatty acids with aliphatic tails of 6-12 carbons, which can form medium-chain triglycerides. Long-chain fatty acids (LCFA) are fatty acids with aliphatic tails 13 to 21 carbons. Very long chain fatty acids (VLCFA) are fatty acids with aliphatic tails longer than 22 carbons. Non-limiting examples of fatty acids include myristoleic acid, palmitoleic acid, sapienic acid, oleic acid, elaidic acid, vaccenic acid, linoleic acid, linoelaidic acid, arachidonic acid, eicosapentaenoic acid, erucic acid, docsahexaenoic acid, caprylic acid, capric acid, lauric acid, myristic acid, palmitic acid, stearic acid, arachidic acid, behenic acid, lignoceric acid, and cerotic acid.

As used herein, the term "failed to respond to a prior therapy" or "refractory to a prior therapy," refers to a cancer that progressed despite treatment with the therapy.

By "level" is meant a level of a cell type, as compared to a reference. The reference can be any useful reference, as defined herein. By a "decreased level" or an "increased level" of a cell type is meant a decrease or increase in cell level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a cell type may be expressed in mass/vol (e.g., g/dL, mg/mL, µg/mL, ng/mL) or percentage relative to total cells in a sample. In some embodiments of any of the foregoing methods, the reference is a sample from a healthy subject such as a subject that does not have cancer. In some embodiments of any of the foregoing methods, the reference is an artificial sample with a level (e.g., a level of MDSCs such as monocytic and/or granulocytic MDSCs or activated T-cells) shown beneficial in the treatment of a disorder.

As used herein, "metastatic nodule" refers to an aggregation of tumor cells in the body at a site other than the site of the original tumor.

As used herein, "metastatic tumor" refers to a tumor or cancer in which the cancer cells forming the tumor have a high potential to or have begun to, metastasize, or spread from one location to another location or locations within a subject, via the lymphatic system or via haematogenous spread, for example, creating secondary tumors within the subject. Such metastatic behavior may be indicative of malignant tumors. In some cases, metastatic behavior may be associated with an increase in cell migration and/or invasion behavior of the tumor cells.

Examples of cancers that can be defined as metastatic include but are not limited to non-small cell lung cancer, breast cancer, ovarian cancer, colorectal cancer, biliary tract cancer, bladder cancer, brain cancer including glioblastomas and medullablastomas, cervical cancer, choriocarcinoma, endometrial cancer, esophageal cancer, gastric cancer, hematological neoplasms, multiple myeloma, leukemia, intraepithelial neoplasms, liver cancer, lymphomas, neuroblastomas, oral cancer, pancreatic cancer, prostate cancer, sarcoma, skin cancer including melanoma, basocellular cancer, squamous cell cancer, testicular cancer, stromal tumors, germ cell tumors, thyroid cancer, and renal cancer.

As used herein, "migrating cancer" refers to a cancer in which the cancer cells forming the tumor migrate and subsequently grow as malignant implants at a site other than the site of the original tumor. The cancer cells migrate via seeding the surface of the peritoneal, pleural, pericardial, or subarachnoid spaces to spread into the body cavities; via invasion of the lymphatic system through invasion of lymphatic cells and transport to regional and distant lymph nodes and then to other parts of the body; via haematogenous spread through invasion of blood cells; or via invasion of the surrounding tissue. Migrating cancers include metastatic tumors and cell migration cancers, such as ovarian cancer, mesothelioma, and primary lung cancer, each of which is characterized by cellular migration.

"Non-metastatic cell migration cancer" as used herein refers to cancers that do not migrate via the lymphatic system or via haematogenous spread.

As used herein, the term "pharmaceutical composition" refers to an active compound, formulated together with one or more pharmaceutically acceptable carriers. In some embodiments, active compound is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

A "pharmaceutically acceptable excipient," as used herein, refers any inactive ingredient (for example, a vehicle capable of suspending or dissolving the active compound) having the properties of being nontoxic and non-inflammatory in a subject. Typical excipients include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Excipients include, but are not limited to: butyated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xyitol. Those of ordinary skill in the art are familiar with a variety of agents and materials useful as excipients.

The term "pharmaceutically acceptable salt," as use herein, refers to those salts of the compounds described here that are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenyipropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethyammonium, methyamine, dimethyamine, trimethyamine, triethylamine, and ethyamine.

"Predetermined level" as used herein, refers to a pre-specified particular level of one or more particular cell type, e.g., MDSCs such as monocytic and/or granulocytic MDSCs or activated T-cells. In some embodiments, a predetermined level is an absolute value or range. In some embodiments, a predetermined level is a relative value. In some embodiments, a predetermined level is the same as or different (e.g., higher or lower than) a level of one or more particular cell type in a reference, e.g., a reference tumor sample, or a level specified in a reference document such as a pharmaceutical specification.

In some embodiments, a predetermined level is an absolute level or range of one or more cell type in a sample. In some embodiments, a predetermined level is a level or range of one or more cell types in a sample relative to total level of cells in the sample. In some embodiments, a predetermined level is a level or range of one or more cell types in a sample relative to total level of cells in the sample. In some embodiments, a predetermined level is expressed as a percent.

"Progression-free survival" as used herein, refers to the length of time during and after medication or treatment during which the disease being treated (e.g., cancer) does not get worse.

"Proliferation" as used in this application involves reproduction or multiplication of similar forms (cells) due to constituting (cellular) elements.

As used herein, "slowing the spread of metastasis" refers to reducing or stopping the formation of new loci; or reducing, stopping, or reversing the tumor load.

As used herein, "slowing the spread of migrating cancer" refers to reducing or stopping the formation of new loci; or reducing, stopping, or reversing the tumor load.

The term "subject," as used herein, refers to a human or non-human animal (e.g., a mammal such as a non-human primate, horse, cow, or dog).

The term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

A "therapeutic regimen" refers to a dosing regimen whose administration across a relevant population is correlated with a desired or beneficial therapeutic outcome.

The term "treatment" (also "treat" or "treating"), in its broadest sense, refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

As used herein, "tumor seeding" refers to the spillage of tumor cell clusters and their subsequent growth as malignant implants at a site other than the site of the original tumor.

The term "PD-1 inhibitor," as used herein, refers to a compound such as an antibody capable of inhibiting the activity of the protein that in humans is encoded by the PDCD1 gene. Known PD-1 inhibitors include nivolumab, pembrolizumab, pidilizumab, BMS 936559, and MPDL3280A.

The term "PD-1 inhibitor," as used herein, refers to a compound such as an antibody capable of inhibiting the activity of the protein that in humans is encoded by the CD274 gene. Known PD-L1 inhibitors include atezolizumab and MED4736.

The term "CTLA-4 inhibitor," as used herein, refers to a compound such as an antibody capable of inhibiting the activity of the protein that in humans is encoded by the CTLA4 gene. Known CTLA-4 inhibitors include ipilimumab.

The term "CSF-1R inhibitors," as used herein refers to a compound such as an antibody capable of inhibiting the activity of the protein that in humans is encoded by the CSF1R gene. Known CSF-1R inhibitors include pexidartinib and AZD6495.

The term "IDO inhibitor," as used herein, refers to a compound such as an antibody capable of inhibiting the activity of the protein that in humans is encoded by the IDO1 gene. Known IDO inhibitors include norharmane, rosmarinic acid, and alpha-methyl-tryptophan.

The term "A1 adenosine inhibitor," as used herein, refers to a compound such as an antibody capable of inhibiting the activity of the protein that in humans is encoded by the ADORA1 gene. Known A1 adenosine inhibitors include 8-cyclopentyl-1,3-dimethyxanthine, 8-cyclopentyl-1,3-dipropyxanthine, 8-phenyl-1,3-dipropylxanthine, bamifylline, BG-9719, BG-9928, FK-453, FK-838, rolofylline, and N-0861.

The term "A2A adenosine inhibitor," as used herein, refers to a compound such as an antibody capable of inhibiting the activity of the protein that in humans is encoded by the ADORA2A gene. Known A2A adenosine inhibitors include ATL-4444, istradefylline, MSX-3, preladenant, SCH-58261, SCH-412,348, SCH-442,416, ST-1535, VER-6623, VER-6947, VER-7835, viadenant, and ZM-241, 385.

The term "A2B adenosine inhibitor," as used herein, refers to a compound such as an antibody capable of inhibiting the activity of the protein that in humans is encoded by the ADORA2B gene. Known A2B adenosine inhibitors include ATL-801, CVT-6883, MRS-1706, MRS-1754, OSIP-339,391, PSB-603, PSB-0788, and PSB-1115.

The term "A3A adenosine inhibitor," as used herein, refers to a compound such as an antibody capable of inhibiting the activity of the protein that in humans is encoded by the ADORA3 gene. Known A3A adenosine inhibitors include KF-26777, MRS-545, MRS-1191, MRS-1220, MRS-1334, MRS-1523, MRS-3777, MRE-3005-F20, MRE-3008-F20, PSB-11, OT-7999, VUF-5574, and SSR161421.

The term "arginase inhibitor," as used herein, refers to a compound capable of inhibiting the activity of a protein that in humans is encoded by the ARG1 or ARG2 genes. Known arginase inhibitors include (2s)-(+)-amino-5-iodoacetamidopentanoic acid, NG-hydroxy-L-arginine, (2S)-(+)-amino-6-iodoacetamidohexanoic acid, and (R)-2-amino-6-borono-2-(2-(piperidin-1-yl)ethyl)hexanoic acid.

The term "HDAC inhibitor," as used herein, refers to a compound such as an antibody that is capable of inhibiting the activity of the protein that is a member of the histone deacetylase class of enzymes, e.g., HDAC1, HDAC2, HDAC3, HDAC4, HDAC5, HDAC6, HDAC7, HDAC8, HDAC9, HDAC10, HDAC11, SIRT1, SIRT2, SIRT3, SIRT4, SIRT5, SIRT6, and SIRT7. Known HDAC inhibitors include valproic acid, SAHA, and romidepsin.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

DETAILED DESCRIPTION OF THE INVENTION

Figure 1:
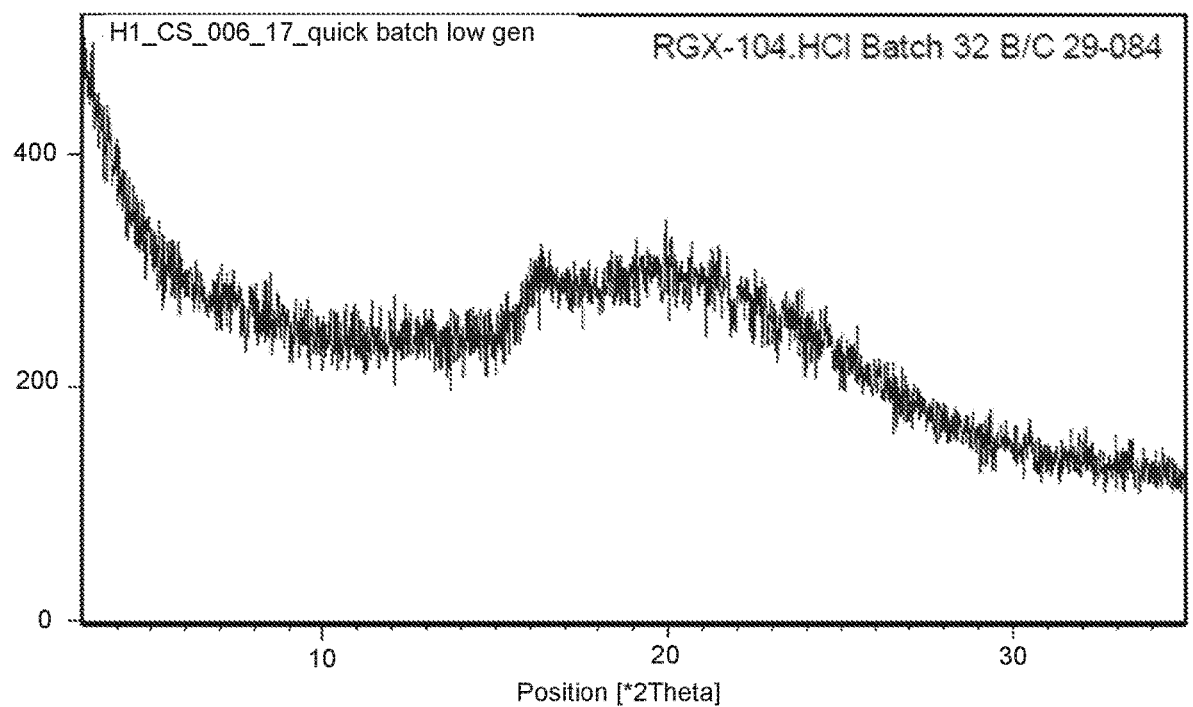
FIG. 1 is an XRPD diffractogram of amorphous compound 1 hydrochloride.

The LXR agonist for which polymorphs were studied is the hydrochloride salt of compound 1:

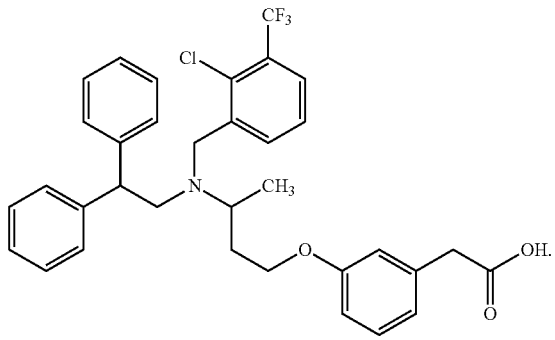 [SMILES: CC(CCOc1cccc(CC(=O)O)c1)N(Cc1cccc(C(F)(F)F)c1Cl)CC(c1ccccc1)c1ccccc1]

1

Initial studies to identify crystalline forms of the hydrochloride salt of compound 1 were unsuccessful. Extensive salt and crystallization studies had been performed using classical techniques, including anti-solvent layering, slow evaporation (at 5° C. and 50° C.), vapor diffusion, various anti-solvent combinations, solid state grinding, temperature cycling, and co-crystallization. The only stable free-flowing solid form that had been isolated was amorphous.

While the amorphous form had adequate pharmaceutical properties for initial studies, a crystalline form with improved physical properties (e.g., reduced hygroscopicity and higher melting point) and an ability, via its crystallization, to purge impurities is highly desired for a pharmaceutical drug substance.

To identify crystalline forms of an LXRβ agonist with improved properties, the present inventors carried out polymorph screening experiments under various conditions using a batch of the hydrochloride salt of compound 1 with higher chemical purity than used in earlier studies. Nine polymorphs were prepared in crystalline forms and their properties assessed. Following identification of a preferred polymorph with optimal properties, larger quantities were prepared for characterization.

As described herein, only one of the nine polymorphs identified is an ansolvate, the other eight are solvates of organic solvents. Utilizing an ansolvate crystalline material in preparation of pharmaceutical formulations can be important to avoid unacceptable levels of organic solvents in the final pharmaceutical formulations.

In some embodiments, a crystalline form of the LXR agonist has one or more (e.g., two or more, three or more, four or more, five or more, six or more, seven or more, eight or more, nine or more, ten or more, eleven or more, twelve or more, thirteen or more, fourteen or more) peaks listed in Table 1 as measured by X-ray powder diffractometry. In some embodiments, the crystalline form of the LXR agonist has all of the peaks listed in Table 1 as measured by X-ray powder diffractometry.

In some embodiments, a crystalline form of the LXR agonist has one or more (e.g., two or more, three or more, four or more, five or more, six or more, seven or more, eight or more, nine or more, ten or more, eleven or more, twelve or more, thirteen or more, fourteen or more) peaks listed in Table 2 as measured by X-ray powder diffractometry. In some embodiments, the crystalline form of the LXR agonist has all of the peaks listed in Table 2 as measured by X-ray powder diffractometry.

TABLE 2

XRPD peak list for a crystalline solvate

| 2θ (°) | Intensity |
|---|---|
| 5.4236 | 41.77 |
| 9.2199 | 14.67 |
| 9.6108 | 57.53 |
| 10.857 | 39.89 |
| 11.6632 | 19.19 |
| 12.1811 | 21.75 |
| 12.4909 | 9.62 |
| 13.5112 | 12.68 |
| 14.8366 | 27.75 |
| 15.004 | 26.3 |
| 15.892 | 62.35 |
| 16.8112 | 57.53 |
| 17.0133 | 32.09 |
| 18.0836 | 84.42 |
| 18.1666 | 69.53 |
| 18.4108 | 29.18 |
| 18.7562 | 81.69 |
| 19.3037 | 64.34 |
| 19.7935 | 33.16 |
| 20.126 | 100 |
| 20.5066 | 25.05 |
| 21.3418 | 28.43 |
| 21.9445 | 29.18 |
| 22.83 | 33.35 |
| 23.3597 | 30.42 |
| 24.5003 | 21.74 |
| 25.4498 | 7.28 |
| 25.7426 | 5.29 |
| 26.1526 | 7.05 |
| 26.4257 | 22.46 |
| 26.7673 | 28.63 |
| 27.1524 | 13.42 |
| 28.3808 | 18.13 |
| 29.1174 | 5.79 |
| 29.5267 | 14.03 |
| 30.4396 | 11.03 |
| 32.237 | 4.72 |
| 32.6826 | 2.3 |

In some embodiments, a crystalline form of the LXR agonist has one or more (e.g., two or more, three or more, four or more, five or more, six or more, seven or more, eight or more, nine or more, ten or more, eleven or more, twelve or more, thirteen or more, fourteen or more) peaks listed in Table 3 as measured by X-ray powder diffractometry. In some embodiments, the crystalline form of the LXR agonist has all of the peaks listed in Table 3 as measured by X-ray powder diffractometry.

TABLE 3

XRPD peak list for a crystalline solvate

| 2θ (°) | Intensity |
|---|---|
| 5.1705 | 33.59 |
| 8.2872 | 19.28 |
| 8.5811 | 16.86 |
| 10.3398 | 12.53 |
| 10.7416 | 6.61 |
| 11.244 | 9.98 |
| 11.5116 | 15.32 |
| 12.3496 | 28.25 |
| 12.8724 | 9.55 |

TABLE 3-continued

XRPD peak list for a crystalline solvate

| 2θ (°) | Intensity |
|---|---|
| 15.002 | 10.87 |
| 15.8279 | 6.45 |
| 16.4179 | 100 |
| 16.6066 | 11.94 |
| 17.2086 | 15.3 |
| 18.1557 | 23.79 |
| 18.4086 | 61.49 |
| 18.8229 | 31.47 |
| 19.2511 | 31.73 |
| 19.6477 | 21.95 |
| 19.9035 | 41.76 |
| 20.2514 | 16.48 |
| 21.5587 | 34.51 |
| 22.6531 | 8.29 |
| 23.1448 | 14.21 |
| 23.4296 | 10.02 |
| 24.055 | 4.82 |
| 24.3096 | 9.26 |
| 24.8405 | 22.02 |
| 25.7579 | 14.2 |
| 26.3886 | 12.04 |
| 26.6976 | 8.78 |
| 27.1659 | 8.11 |
| 27.9796 | 6.46 |
| 28.2912 | 3.59 |
| 29.9362 | 5.61 |
| 30.8553 | 3.87 |
| 31.823 | 2.96 |
| 33.1641 | 3.08 |
| 33.5846 | 2.54 |
| 34.1776 | 1.8 |

In some embodiments, a crystalline form of the LXR agonist has one or more (e.g., two or more, three or more, four or more, five or more, six or more, seven or more, eight or more, nine or more, ten or more, eleven or more, twelve or more, thirteen or more, fourteen or more) peaks listed in Table 4 as measured by X-ray powder diffractometry. In some embodiments, the crystalline form of the LXR agonist has all of the peaks listed in Table 4 as measured by X-ray powder diffractometry.

TABLE 4

XRPD peak list for a crystalline solvate

| 2θ (°) | Intensity |
|---|---|
| 7.8996 | 11.92 |
| 9.1319 | 1.56 |
| 10.5922 | 11.44 |
| 11.2463 | 17.21 |
| 11.48 | 27.96 |
| 12.3593 | 10.18 |
| 13.0627 | 19.36 |
| 13.7113 | 27.98 |
| 14.0362 | 52.76 |
| 15.8167 | 37.7 |
| 16.0494 | 15.58 |
| 16.7107 | 63.2 |
| 17.9404 | 37.22 |
| 18.5089 | 84.41 |
| 19.0529 | 29.76 |
| 19.6097 | 27.3 |
| 20.1798 | 100 |
| 21.2573 | 52.09 |
| 21.6718 | 28.35 |
| 22.6359 | 12.4 |
| 23.0962 | 19.77 |
| 24.1434 | 27.09 |
| 24.9147 | 23.1 |
| 25.3111 | 9.55 |
| 25.9516 | 11.11 |

TABLE 4-continued

XRPD peak list for a crystalline solvate

| 2θ (°) | Intensity |
|---|---|
| 26.3867 | 6.78 |
| 26.8241 | 4.1 |
| 27.6819 | 10.13 |
| 28.4093 | 16.72 |
| 28.8739 | 11.56 |
| 29.8259 | 7.95 |
| 30.283 | 3.23 |
| 31.2164 | 3.73 |

In some embodiments, a crystalline form of the LXR agonist has one or more (e.g., two or more, three or more, four or more, five or more, six or more, seven or more, eight or more, nine or more, ten or more, eleven or more, twelve or more, thirteen or more, fourteen or more) peaks listed in Table 5 as measured by X-ray powder diffractometry. In some embodiments, the crystalline form of the LXR agonist has all of the peaks listed in Table 5 as measured by X-ray powder diffractometry.

TABLE 5

XRPD peak list for a crystalline solvate

| 2θ (°) | Intensity |
|---|---|
| 5.4025 | 8.86 |
| 8.3396 | 22.38 |
| 9.6182 | 66.01 |
| 10.8536 | 19.6 |
| 11.5312 | 20.78 |
| 12.1995 | 62.48 |
| 12.6698 | 12.59 |
| 13.2627 | 16.08 |
| 14.6927 | 30.63 |
| 14.9715 | 6.34 |
| 15.9249 | 85.03 |
| 16.8423 | 59.14 |
| 18.0239 | 68.58 |
| 18.1986 | 35.76 |
| 18.4546 | 41.88 |
| 18.5958 | 38.01 |
| 18.972 | 40.44 |
| 19.3477 | 19.16 |
| 19.4898 | 23.95 |
| 20.0845 | 45.84 |
| 20.2224 | 100 |
| 20.4368 | 80.22 |
| 21.0886 | 31.79 |
| 21.4269 | 24.17 |
| 22.8942 | 24.72 |
| 23.0645 | 34.41 |
| 23.2622 | 31.06 |
| 23.5395 | 22.33 |
| 24.5785 | 49.25 |
| 24.6437 | 48.13 |
| 25.0207 | 12.18 |
| 25.2721 | 12.76 |
| 25.4819 | 11.53 |
| 25.8943 | 13.67 |
| 26.5055 | 23.63 |
| 26.7802 | 19.01 |
| 26.9945 | 17.77 |
| 27.8854 | 6.97 |
| 28.3481 | 8.26 |
| 28.591 | 10.17 |
| 29.2006 | 13.53 |
| 29.4914 | 14.14 |
| 29.7283 | 12.92 |
| 29.9743 | 11.46 |
| 30.5259 | 9.57 |
| 31.1207 | 8.72 |
| 31.8849 | 5.15 |
| 32.2923 | 15.78 |

TABLE 5-continued

XRPD peak list for a crystalline solvate

| 2θ (°) | Intensity |
|---|---|
| 34.1302 | 10.05 |
| 23.0645 | 34.41 |

In some embodiments, a crystalline form of the LXR agonist has one or more (e.g., two or more, three or more, four or more, five or more, six or more, seven or more, eight or more, nine or more, ten or more, eleven or more, twelve or more, thirteen or more, fourteen or more) peaks listed in Table 6 as measured by X-ray powder diffractometry. In some embodiments, the crystalline form of the LXR agonist has all of the peaks listed in Table 6 as measured by X-ray powder diffractometry.

TABLE 6

XRPD peak list for a crystalline solvate

| 2θ (°) | Intensity |
|---|---|
| 5.9433 | 32.92 |
| 8.0521 | 11.26 |
| 9.5618 | 51.87 |
| 10.5492 | 3.75 |
| 10.998 | 13.28 |
| 11.9473 | 38.06 |
| 12.088 | 88.38 |
| 12.9525 | 37.1 |
| 13.6803 | 8.98 |
| 14.9727 | 70.19 |
| 16.1227 | 18.17 |
| 16.6537 | 14.56 |
| 17.0476 | 100 |
| 17.8773 | 22.57 |
| 18.3732 | 58.84 |
| 19.0792 | 28.08 |
| 19.2332 | 37.66 |
| 19.5113 | 46.05 |
| 20.3608 | 50.14 |
| 20.5317 | 75.37 |
| 21.2366 | 12.7 |
| 22.1327 | 43.3 |
| 22.4824 | 25.43 |
| 22.9241 | 24.57 |
| 23.4169 | 20.33 |
| 24.1594 | 25.47 |
| 24.3758 | 32.46 |
| 24.563 | 23.71 |
| 25.0188 | 7.83 |
| 25.6015 | 36.84 |
| 26.0836 | 14.03 |
| 26.9014 | 9.64 |
| 27.3631 | 11.03 |
| 27.5173 | 6.47 |
| 27.9237 | 4.39 |
| 28.1861 | 18.43 |
| 28.5123 | 4.39 |
| 28.9541 | 8.59 |
| 29.6732 | 9.28 |
| 29.8252 | 9.33 |
| 30.2614 | 5.41 |
| 31.5823 | 9.96 |
| 32.1308 | 7.08 |
| 32.7993 | 4 |
| 33.647 | 8.59 |
| 34.049 | 5.24 |
| 34.5802 | 3.59 |

In some embodiments, a crystalline form of the LXR agonist has one or more (e.g., two or more, three or more, four or more, five or more, six or more, seven or more, eight or more, nine or more, ten or more, eleven or more, twelve or more, thirteen or more, fourteen or more) peaks listed in Table 7 as measured by X-ray powder diffractometry. In some embodiments, the crystalline form of the LXR agonist has all of the peaks listed in Table 7 as measured by X-ray powder diffractometry.

TABLE 7

XRPD peak list for a crystalline solvate

| 2θ (°) | Intensity |
|---|---|
| 16.0035 | 27.87 |
| 16.9202 | 100 |
| 18.0666 | 8.56 |
| 19.4175 | 5.18 |
| 20.5555 | 14.62 |
| 24.6772 | 9.38 |
| 24.7186 | 11.49 |
| 26.5782 | 2.82 |
| 27.0604 | 0.66 |
| 28.5352 | 5.36 |
| 32.383 | 1.56 |
| 32.8583 | 0.57 |
| 34.2504 | 2.34 |
| 34.34 | 1.76 |

In some embodiments, a crystalline form of the LXR agonist has one or more (e.g., two or more, three or more, four or more, five or more, six or more, seven or more, eight or more, nine or more, ten or more, eleven or more, twelve or more, thirteen or more, fourteen or more) peaks listed in Table 8 as measured by X-ray powder diffractometry. In some embodiments, the crystalline form of the LXR agonist has all of the peaks listed in Table 8 as measured by X-ray powder diffractometry.

TABLE 8

XRPD peak list for a crystalline solvate

| 2θ (°) | Intensity |
|---|---|
| 5.4247 | 24.22 |
| 8.3801 | 3.94 |
| 9.2935 | 2.79 |
| 9.5803 | 28.78 |
| 10.9063 | 18.27 |
| 11.5241 | 20.13 |
| 12.1976 | 21.15 |
| 12.7031 | 3.18 |
| 13.287 | 7.19 |
| 14.7757 | 9.23 |
| 14.9958 | 6.06 |
| 15.8018 | 38.25 |
| 16.7577 | 28.36 |
| 17.9299 | 100 |
| 18.2267 | 22.32 |
| 18.3993 | 14.54 |
| 18.6474 | 13.69 |
| 19.0276 | 29.35 |
| 19.2709 | 17.69 |
| 19.5926 | 10.82 |
| 20.3109 | 76.05 |
| 21.1566 | 10.17 |
| 21.5046 | 9.84 |
| 21.7386 | 4.83 |
| 22.8957 | 4.76 |
| 23.1874 | 24.13 |
| 23.7093 | 6.12 |
| 24.5381 | 12.17 |
| 25.315 | 6.96 |
| 25.6519 | 5.13 |
| 26.4305 | 9.67 |
| 26.6511 | 12 |
| 27.0082 | 13.06 |
| 27.3902 | 3.81 |
| 28.1539 | 5.65 |

TABLE 8-continued

XRPD peak list for a crystalline solvate

| 2θ (°) | Intensity |
|---|---|
| 28.7303 | 3.48 |
| 29.1083 | 2.91 |
| 29.391 | 4.81 |
| 29.6114 | 3.99 |
| 29.9 | 2.69 |
| 30.109 | 6.07 |
| 30.4424 | 4.19 |
| 31.1403 | 2.43 |
| 31.9691 | 5.62 |
| 32.5343 | 7.88 |
| 34.2063 | 3.85 |
| 34.6886 | 2.59 |

In some embodiments, a crystalline form of the LXR agonist has one or more (e.g., two or more, three or more, four or more, five or more, six or more, seven or more, eight or more, nine or more, ten or more, eleven or more, twelve or more, thirteen or more, fourteen or more) peaks listed in Table 9 as measured by X-ray powder diffractometry. In some embodiments, the crystalline form of the LXR agonist has all of the peaks listed in Table 9 as measured by X-ray powder diffractometry.

TABLE 9

XRPD peak list for a crystalline solvate

| 2θ (°) | Intensity |
|---|---|
| 5.0351 | 50.92 |
| 8.5667 | 20.31 |
| 10.0824 | 23.45 |
| 11.1547 | 18.24 |
| 11.613 | 17.67 |
| 11.872 | 8.5 |
| 12.6633 | 11.12 |
| 13.0186 | 13.16 |
| 13.8753 | 52.49 |
| 15.0358 | 8.2 |
| 16.3866 | 62.65 |
| 16.5989 | 32.87 |
| 17.1831 | 33.58 |
| 18.3804 | 47.75 |
| 19.129 | 100 |
| 19.5267 | 28.55 |
| 19.9338 | 16.26 |
| 20.2409 | 4.87 |
| 20.8318 | 27.06 |
| 21.0606 | 35.27 |
| 21.8711 | 8.06 |
| 22.4128 | 32.71 |
| 23.3863 | 19.54 |
| 23.9362 | 22.59 |
| 24.2514 | 5.53 |
| 24.9774 | 3.83 |
| 25.2247 | 11.17 |
| 25.4502 | 7.87 |
| 25.6575 | 11.52 |
| 26.2094 | 27.96 |
| 26.6334 | 20.75 |
| 26.8767 | 5.13 |
| 27.3168 | 7.63 |
| 27.5103 | 9.47 |
| 27.8865 | 7.85 |
| 29.1615 | 4.45 |
| 30.3428 | 13.78 |
| 30.6434 | 3.74 |
| 31.051 | 2.37 |
| 31.5808 | 1.67 |
| 32.5635 | 2.68 |
| 33.2288 | 4.3 |

Formulations

The compositions described herein may be used in, or methods to produce, formulations comprising the compound:

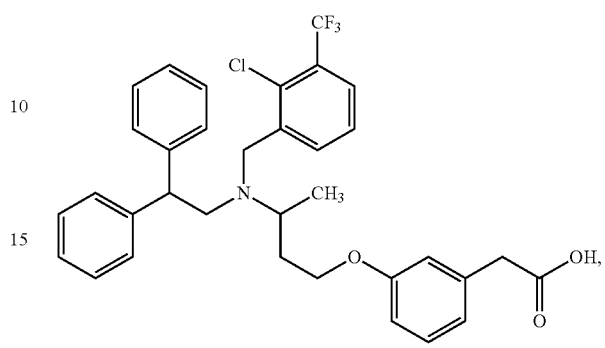

or pharmaceutically acceptable salts thereof.

In some embodiments, the formulations include a fatty acid. In some embodiments, the fatty acid is a long chain fatty acid carboxyate, e.g., a saturated fatty acid carboxyate selected from caprylate, caprate, palmitate, laurate, and/or stearate or an unsaturated fatty acid carboxyate selected from myristoelate, palmitoleate, sapienate, oleate, linoleate, elaidate, and/or vaccenate. In some embodiments, the fatty acid is oleate.

Non-limiting examples of suitable lipids that can be useful in the formulations of the invention include glycerol fatty acid esters such as glycerol linoleates, glycerol stearates, glycerol oleates, glycerol ethyihexanoates, glycerol capryrates, glycerol behenates, and glycerol laurates. Glycerol Esters of Fatty Acids, as known in the art, are esters of fatty acids and glycerol or polyglycerol and their derivatives. Glycerol Esters of Fatty Acids include glycerol fatty acid ester, glycerol acetic acid fatty acid ester, glycerol lactic acid fatty acid ester, glycerol citric acid fatty acid ester, glycerol succinic acid fatty acid ester, glycerol diacetyl tartaric acid fatty acid ester, glycerol acetic acid ester, polyglycerol fatty acid ester, and polyglycerol condensed ricinoleic acid ester.

In some embodiments, the formulation comprises any of the foregoing pharmaceutically acceptable salts; a buffering agent (e.g., a lipid soluble carboxylic acid such as sodium oleate); and a lipophilic vehicle, wherein the lipophilic vehicle comprises: a lipid excipient (e.g., a lipid excipient comprising a monoglyceride, a diglyceride, and/or a triglyceride such as glycerol linoleate); and/or a surfactant (e.g., a surfactant comprising at least one polyglycolized glyceride such as lauroyl macrogol-32 glyceride).

In some embodiments, the formulation further includes a stabilizing agent, e.g., a stabilizing agent including EDTA (ethylenediaminetetraacetic acid), sodium citrate, BHA (butylated hydroxyanisole), and/or BHT (butylated hydroxytoluene).

In some embodiments, the formulation is a semi-solid suspension. In some embodiments, the formulation is self-emulsifying. In some embodiments, the formulation is formulated for oral administration.

In some embodiments, the formulation, the lipid excipient content of the lipophilic vehicle is about 40% by weight to about 80% by weight; the surfactant content of the lipophilic vehicle is about 20% by weight to about 60% by weight; about 0.2% by weight to about 5% by weight of the formulation is lipid-soluble carboxylic acid salt; and an amount of the pharmaceutically acceptable salt is about 2% by weight to about 10% by weight of the formulation. In some embodiments, the formulation further includes about 0.2% to 2% by weight of the stabilizing agent.

In some embodiments, the pH of the formulation is from about 4 and to about 8, e.g., from about 5 and to about 7.

In some embodiments, the formulation has increased bioavailability upon oral administration compared with a formulation comprising a structure of formula I wherein $Z^\ominus$ is an inorganic salt, e.g., a chloride salt. For example, in some embodiments, the formulation has increased bioavailability upon oral administration compared with a formulation comprising a structure of formula I wherein $Z^\ominus$ is the hydrochloride salt and the hydrochloride salt is formulated as described in Collins et al. J. Med. Chem., 2002, 45:1963-1966, the formulation methods of which are herein incorporated by reference.

In some embodiments, an amount of the pharmaceutically acceptable in the formulation decreases by less than about 2% after storage for 1 week, 3 weeks, 3 months, or 6 months at a temperature of 40° C. and a relative humidity of 75%.

In some embodiments, the formulation is formulated as a capsule. In some embodiments, the capsule is a gelatin capsule, e.g., a hard gelatin capsule or a soft gelatin capsule, such as an HPMC (hydroxypropyl methylcellulose) capsule or a non-gelatin soft shell capsule.

The compositions of the invention may be used in methods to produce any of the foregoing formulations. In some embodiments, the methods include dissolving the compound, or a pharmaceutically acceptable salt thereof, in the lipophilic vehicle. In some embodiments, the method further includes adding a sodium salt of a fatty acid. In some embodiments, the sodium salt of a fatty acid is added to the lipophilic vehicle before the compound of formula II, or the pharmaceutically acceptable salt thereof. In some embodiments, sodium chloride precipitates upon addition of the sodium salt of a fatty acid. In some embodiments, the method further includes adding a stabilizing agent. In some embodiments, the lipophilic vehicle comprises at least one glycerol fatty acid ester, e.g., glycerol linoleate. In some embodiments, the lipophilic vehicle comprises at least one polyglycolized glyceride, e.g., lauroyl macrogol-32 glyceride. In some embodiments, the stabilizing agent comprises EDTA and/or sodium citrate.

If the form of the compound used in the formulation is a salt (e.g., a protonated form such as the hydrochloride salt), at least 1.1 molar equivalents of lipid-soluble carboxylic acid salt with respect to the compound may be included in the formulation. For instance, about 1.1 molar equivalents to about 3 molar equivalents, about 1.1 molar equivalents to about 2 molar equivalents, about 1.1 molar equivalents to about 1.5 molar equivalents, about 1.5 molar equivalents to about 3 molar equivalents, or about 1.5 molar equivalents to about 2 molar equivalents. Without wishing to be bound by a particular theory, it is thought that the first equivalent of lipid-soluble carboxylic acid salt effects an ion exchange with the protonated compound (e.g., the chloride of the hydrochloride salt exchanges with the carboxyate of the lipid-soluble carboxylic acid salt such as the oleate ion in sodium oleate) and the other amount equilibrates with the carboxylic acid group of the compound to form a buffer system.

Preferably, to achieve better stability, the pH of the formulation is at least about 4. For instance, the pH can be about 4 to about 8, about 4 to about 7, about 4 to about 6, about 5 to about 8, about 5 to about 7, about 5 to about 6. It has been found that achieving such pH values can lead to reduced degradation of the compound of formula II during storage of the formulation. Preferably, the pH of the formulation is about 5 to about 7. The term "pH" as used herein refers to the apparent pH that is the pH measured using pH paper (e.g. MColorpHast™ pH 0-6.0 or Universal Indicator 0-14) by the following procedure: the pH paper is wetted with water, a drop (approximately 20 μL) of the formulation is applied to pH paper, and the color change is compared to the pH color chart of the pH paper manufacturer.

In some embodiments the surfactant is a polyglycolized glyceride. By "polyglycolized glyceride" is meant a polyethylene glycol glyceride monoester, a polyethyene glycol glyceride diester, a polyethyene glycol glyceride triester, or a mixture thereof containing a variable amount of free polyethylene glycol, such as a polyethyene glycol-oil transesterification product. The polyglycolized glyceride can include either monodisperse (i.e., single molecular weight) or polydisperse polyethyene glycol moieties of a predetermined size or size range (e.g., PEG2 to PEG 40). Polyethyene glycol glycerides include, for example: PEG glyceryl caprate, PEG glyceryl capryate, PEG-20 glyceryl laurate (Tagat® L, Goldschmidt), PEG-30 glyceryl laurate (Tagat® L2, Goldschmidt), PEG-15 glyceryl laurate (Glycerox L series, Croda), PEG-40 glyceryl laurate (Glycerox L series, Croda), PEG-20 glyceryl stearate (Capmul® EMG, ABITEC), and Aldo@ MS-20 KFG, Lonza), PEG-20 glyceryl oleate (Tagat® O, Goldschmidt), and PEG-30 glyceryl oleate (Tagat® O2, Goldschmidt). Caprylocapryl PEG glycerides include, for example, caprylic/capric PEG-8 glyceride (Labrasol®, Gattefosse), caprylic/capric PEG-4 glyceride (Labrafac® Hydro, Gattefosse), and caprylic/capric PEG-6 glyceride (SOFTIGE® N767, Huls). Oleoyl PEG glyceride include, for eaxmaple oleoyl PEG-6 glyceride, (Labrafil M1944 CS, Gattefosee). Lauroyl PEG glycerides includes, for example, lauroyl PEG-32 glyceride (Gelucire® ELUCIRE 44/14, Gattefosse). Stearoyl PEG glycerides include, for example stearoyl PEG-32 glyceride (Gelucrire 50/13, Gelucire 53/10, Gattefosse). PEG castor oils include PEG-3 castor oil (Nikkol CO-3, Nikko), PEG-5, 9, and 16 castor oil (ACCONON CA series, ABITEC), PEG-20 castor oil, (Emalex C-20, Nihon Emulsion), PEG-23 castor oil (Emulgante EL23), PEG-30 castor oil (Incrocas 30, Croda), PEG-35 castor oil (Incrocas-35, Croda), PEG-38 castor oil (Emulgante EL 65, Condea), PEG-40 castor oil (Emalex C-40, Nihon Emulsion), PEG-50 castor oil (Emalex C-50, Nihon Emulsion), PEG-56 castor oil (Eumulgin® PRT 56, Pulcra SA), PEG-60 castor oil (Nikkol CO-60TX, Nikko), PEG-100 castor oil, PEG-200 castor oil (Eumulgin® PRT 200, Pulcra SA), PEG-5 hydrogenated castor oil (Nikkol HCO-5, Nikko), PEG-7 hydrogenated castor oil (Cremophor W07, BASF), PEG-10 hydrogenated castor oil (Nikkol HCO-10, Nikko), PEG-20 hydrogenated castor oil (Nikkol HCO-20, Nikko), PEG-25 hydrogenated castor oil (Simulsol®1292, Seppic), PEG-30 hydrogenated castor oil (Nikkol HCO-30, Nikko), PEG-40 hydrogenated castor oil (Cremophor RH 40, BASF), PEG-45 hydrogenated castor oil (Cerex ELS 450, Auschem Spa), PEG-50 hydrogenated castor oil (Emalex HC-50, Nihon Emulsion), PEG-60 hydrogenated castor oil (Nikkol HCO-60, Nikko), PEG-80 hydrogenated castor oil (Nikkol HCO-80, Nikko), and PEG-100 hydrogenated castor oil (Nikkol HCO-100, Nikko). Additional polyethylene glycol-oil transesterification products include, for example, stearoyl PEG glyceride (Gelucire®50/13, Gattefosse). The polyglycolized glycerides useful in the formulations of the invention can include polyethylene glycol glyceride monoesters, diesters, and/or triesters of acetic, propionic, butyric, valeric, hexanoic, heptanoic, caprylic, nonanoic, capric, lauric, myristic, palmitic, heptadecanoic, stearic, arachidic, behenic, lignoceric, α-linolenic, stearidonic, eicosapentaenoic, docosahexaenoic, linoleic, γ-linolenic, dihomo-γ-linolenic, arachidonic, oleic, elaidic, eicosenoic, erucic, or nervonic acid, or mixtures thereof. The polyglycol moiety in a polyglycolized glyceride can be polydisperse; that is, they can have a variety of molecular weights. Examples of suitable surfactants include fatty acid macrogol-32 glycerides, such as lauroyl macrogol-32 glycerides (lauroyl polyoxylglycerides). Commercial sources of lauroyl macrogol-32 glycerides include Gelucire 44-14 from Gattefosse. The surfactant (or mixture of surfactants) may be capable of promoting formation of an emulsion upon contact of the formulation with gastrointestinal fluids. In one embodiment, the surfactant is about 20% by weight to about 60% by weight of the lipophilic vehicle. In other embodiments, the surfactant may be about 80% by weight to about 100% by weight of the lipophilic vehicle. In some embodiments, a surfactant can serve a dual role by both dissolving the compound of formula II, or its pharmaceutically acceptable salt, and acting as a surfactant.

Other stabilizing agents include, for example, TPGS compounds and EDTA. EDTA may be used as its sodium salt, disodium-EDTA. These stabilizing agents can help to reduce degradation of the compound of formula II during storage due to processes such as oxidation. Chelating agents such as EDTA are also thought to slow degradation by chelating metal ions that can catalyze the oxidation of the compound of formula II. A TPGS compound may be included at about 5% by weight to about 25% by weight of the formulation. EDTA may be included at about 0.1% by weight to about 2% by weight of the formulation, or about 0.1% by weight to about 1% by weight of the formulation. By "TPGS compound" is meant a compound or mixture of compounds containing one or more vitamin E moieties (e.g., a tocopherol, tocomonoenol, tocodienol, or tocotrienol) bonded to (e.g., by an ester, amide, or thioester bond) to one or more polyethylene glycol (PEG) moieties via a linker (e.g., a dicarboxylic or tricarboxylic acid). The vitamin E moiety can be any naturally occurring or synthetic form of vitamin E, including α-, β-, γ-, and δ-isoforms and all stereoisomers of tocopherol, tocomonoenol, tocodienol, and tocotrienol. Linkers include, for example, dicarboxylic acids (e.g., succinic acid, sebacic acid, dodecanedioic acid, suberic acid, or azelaic acid, citraconic acid, methylcitraconic acid, itaconic acid, maleic acid, glutaric acid, glutaconic acid, fumaric acids and phthalic acids). Exemplary tocopherol polyethylene glycol diesters are TPGS, tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methylcitraconate polyethylene glycol, tocopherol itaconate polyethylene glycol, tocopherol maleate polyethylene glycol, tocopherol glutarate polyethylene glycol, tocopherol glutaconate polyethylene glycol, and tocopherol phthalate polyethylene glycol. Each of the PEG moieties of the TPGS compound can be any polyethylene glycol or any PEG derivative, and can have a molecular weight of 200-6000 kDa (e.g., 400-4000 kDa, 500-2000 kDa, 750-1500 kDa, 800-1200 kDa, 900-1100 kDa, or about 1000 kDa). The PEG moieties can be polydisperse; that is, they can have a variety of molecular weights. PEG derivatives include, for example, methylated PEG, propylene glycol, PEG-NHS, PEG-aldehyde, PEG-SH, PEG-NH$_2$, PEG-CO$_2$H, PEG-OMe and other ethers, branched PEGs, and PEG copolymers (e.g., PEG-b-PPG-b-PEG-1100, PEG-PPG-PEG-1900, PPG-PEG-MBE-1700, and PPG-PEG-PPG-2000). Any known source of TPGS compound can be used in the present invention. An exemplary TPGS compound is tocopheryl PEG-1000 succinate (TPGS-1000), which has a PEG moiety having a molecular weight of 1000 kDa. A food grade TPGS-1000 is available, for example, under the trade name Eastman Vitamin E TPGS® (Eastman Chemical Company, Kingsport, Tenn.). This TPGS is water-soluble form of natural-source vitamin E, which is prepared by esterification of crystalline D-α-tocopheryl acid succinate with polyethylene glycol 1000 (PEG 1000), and contains between 260 and 300 mg/g total tocopherol. Another exemplary TPGS compound is Water Soluble Natural Vitamin E (ZMC-USA, The Woodlands, Tex.). Methods of preparing TPGS are described in U.S. Pat. Nos. 2,680,749 and 3,102,078 and in U.S. Publication Nos. 2007/0184117 and 2007/0141203, which are herein incorporated by reference. TPGS compounds also include TPGS analogs that differ in chemical composition from TPGS by the substitution, addition, or removal of one or more atoms, methylene $(CH_2)_n$ units, or functional groups. TPGS analogs also include include chromanol derivatives (e.g., 6-chromanol PEG-1000 succinate and 6-chromanol PEG-400 succinate), steroid derivatives (e.g., cholesteryl PEG-1000 succinate, cholic acid PEG-1000, dihydro cholic acid PEG-1000, litho-cholic acid PEG-1000, ursodeoxycholic acid PEG-1000, chenodeoxycholic acid PEG-1000), and others (e.g., indomethacin PEG-1000, chromone-2-carboxylic acid PEG-1000, chromone-2-carboxylic acid PEG-1100-OMe, chromone-2-carboxylic acid PEG-1500, chromone-2-carboxylic acid PEG-2000, naproxen PEG-1000, probenecid PEG-1000, 7-carboxymethoxy-4-methyl-coumarin PEG-1000, 5-(4-chlorophenyl)-2-furoic acid PEG-1000, probenecid tocopheryl PEG-1000 succinate, lithocholic acid PEG-1000, and chromone-3-carboxylic acid PEG-1000, 7-hydroxy-coumarinyl-4-acetic acid PEG-1000).

Methods of Treatment

The methods described here can be used to treat cancer.

Treating cancer can result in a reduction in size or volume of a tumor. For example, after treatment, tumor size is reduced by 5% or greater (e.g., 10%, 20%, 30%, 40%, 50%, 60%, 70%, 80%, 90% or greater) relative to its size prior to treatment. Size of a tumor may be measured by any reproducible means of measurement. The size of a tumor may be measured as a diameter of the tumor or by any reproducible means of measurement.

Treating cancer may further result in a decrease in number of tumors. For example, after treatment, tumor number is reduced by 5% or greater (e.g., 10%, 20%, 30%, 40%, 50%, 60%, 70%, 80%, 90% or greater) relative to number prior to treatment. Number of tumors may be measured by any reproducible means of measurement. The number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. The number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with the compound of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with the compound of the invention. A decrease in the mortality rate of a population may also be measured, for example, by calculating for a population the average number of disease-related deaths per unit time following completion of a first round of treatment with the compound of the invention.

Treating cancer can also result in an increased average progression-free survival time of a population of treated subjects in comparison to an untreated population. For example the average progression-free survival time is increased by more than 30 days (more than 60 days, 90 days, or 120 days). An increase in average progression-free survival time of a population may be measured by any reproducible means. An increase in average progression-free survival time of a population may be measured, for example, by calculating for a population the average length of progression-free survival following initiation of treatment with the compound of the invention. An increase in average progression-free survival time of a population may also be measured, for example, by calculating for a population the average length of progression-free survival following completion of a first round of treatment with the compound of the invention.

In some embodiments, the methods described herein may be useful for the treatment of infections such as bacterial infections, parasitic infections, or fungal infections. Compounds of the present invention may be administered by any appropriate route for treatment or prophylactic treatment of a disease or condition associated with an infection. These may be administered to humans, domestic pets, livestock, or other animals with a pharmaceutically acceptable diluent, carrier, or excipient. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Combination Therapies

In some embodiments of the methods described herein, the pharmaceutical composition may further include an additional compound having antiproliferative activity.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

By "antiproliferative agent" is meant any antiproliferative agent which can be used in combination with a LXR agonist to treat the medical conditions recited herein. Antiproliferative agents also include organo-platine derivatives, naphtoquinone and benzoquinone derivatives, chrysophanic acid and anthroquinone derivatives thereof.

EXAMPLES

Example 1. Methods

Polymorph Screening

Bench scale crystallization screening experiments were carried out investigating cooling, temperature cycling, evaporation, anti-solvent addition and seeding techniques. Examples of procedures used include the following:

Temperature cycling crystallizations were carried out using 21 different solvent systems. A mixture of amorphous compound 1 HCl, solvent and anti-solvent were cycled between 40° C. and 5° C. for 72 hours at 0.29° C./minute with 2 hour holds at 40° C. and 5° C.

Evaporative crystallizations were conducted by allowing the saturated solutions from the temperature cycling experiments to evaporate at laboratory ambient temperature (about 22° C.) and pressure. Anti-solvent addition crystallizations used saturated solutions from temperature cycling experiments and heptane or MTBE as anti-solvents.

Cooling followed by anti-solvent addition crystallizations were carried out using 10 solvent/antisolvent mixtures. The material was dissolved in a range of solvents at ambient temperature (about 22° C.). The clear solutions were cooled down to about 5° C., then anti-solvents, heptane and water, were added to the respective solvents. The crystallizations were temperature cycled between about 5° C. and about 22° C. at 0.1° C./minute.

Anti-solvent addition followed by cooling crystallizations were carried out using 23 solvent/antisolvent mixtures. The material was dissolved in ethanol, methanol, 2-propanol, THF, acetonitrile, dioxane, MEK and DCM at about 22° C. Anti-solvent, water, MTBE, toluene, DIPE and heptane was added at about 22° C. where clear solutions, turbidity, or precipitations were observed. The crystallizations were cooled down to about 5° C.

X-Ray Powder Diffraction (XRPD)

XRPD analysis was carried out on a PANalytical X'pert pro, scanning the samples between 3 and 35° 2θ. The material was gently ground to release any agglomerates and loaded onto a multi-well plate with Mylar polymer film to support the sample. The multi-well plate was then placed into the diffractometer and analyzed using Cu K radiation (α1 λ=1.54060 A; α2=1.54443 A; β=1.39225 A; α1: α2 ratio=0.5) running in transmission mode (step size 0.0130 °2θ) using 40 kV/40 mA generator settings.

Polarized Light Microscopy (PLM)

The presence of birefringence was determined using an Olympus BX50 polarizing microscope, equipped with a Motic camera and image capture software (Motic Images Plus 2.0). All images were recorded using the 20× objective.

Thermogravimetric/Differential Thermal Analysis (TG/DTA)

Approximately 5 mg of material was weighed into an open aluminum pan and loaded into a simultaneous thermogravimetric/differential thermal analyzer (TG/DTA) and held at room temperature. The sample was then heated, under a nitrogen purge, at a rate of 10° C./min from 20° C. to 300° C. during which time the change in sample weight was recorded along with any differential thermal events (DTA).

Differential Scanning Calorimetry (DSC)

Approximately 5 mg of material was weighed into an aluminum DSC pan and sealed with a pierced aluminum lid. The sample pan was then loaded into a Seiko DSC6200 and held at 20° C. Once a stable heat-flow response was obtained, the sample and reference were heated/cooled, under a nitrogen purge, by using the following temperature programs and the resulting heat flow response monitored.

Program 1

Heated 20° C. to 130° C. at 10° C./minute held at 130° C. for 5 minutes,

Cooled 130° C. to −20° C. at 100° C./minute, held at −20° C. for 10 minutes,

Heated −20° C. to 130° C. at 10° C./minute held at 130° C. for 10 minutes.

Program 2

Heated 20° C. to 250° C. at 10° C./minute.

Karl Fischer Coulometric Titration (KF)

Approximately 10 mg of solid material was accurately weighed into a vial. The solid was then dissolved in about 1 mL or 5 mL of pre-titrated Hydranal solution, sonicating for about 5-10 min. The solution was manually introduced into the titration cell of a Mettler Toledo C30 Compact Titrator and the weight of the solid entered on the instrument.

$^1$H Nuclear Magnetic Resonance Spectroscopy ($^1$H NMR)

$^1$H-NMR spectroscopic experiments were performed on a Bruker AV500 (frequency: 500 MHz). Experiments were performed in CDCl$_3$ and each sample was prepared to about 10 mM concentration.

Dynamic Vapor Sorption (DVS)

Approximately, 10-20 mg of sample was placed into a mesh vapor sorption balance pan and loaded into a DVS Advantage dynamic vapor sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

High Performance Liquid Chromatography-Ultraviolet Detection (HPLC-UV)

The HPLC method uses a C18 column with an acetonitrile/water/HFA gradient.

Example 2. Characterization of Amorphous HCl Salt of Compound 1

Figure 2:
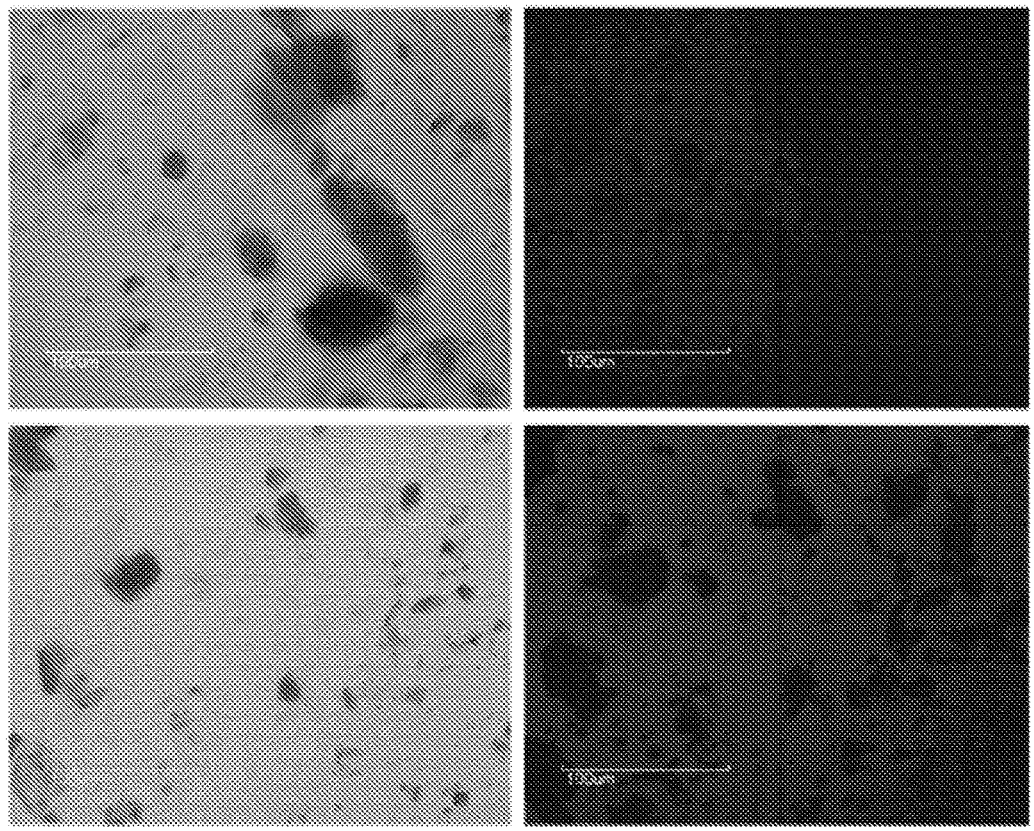
FIG. 2 is a PLM image of amorphous compound 1 hydrochloride.
Figure 3:
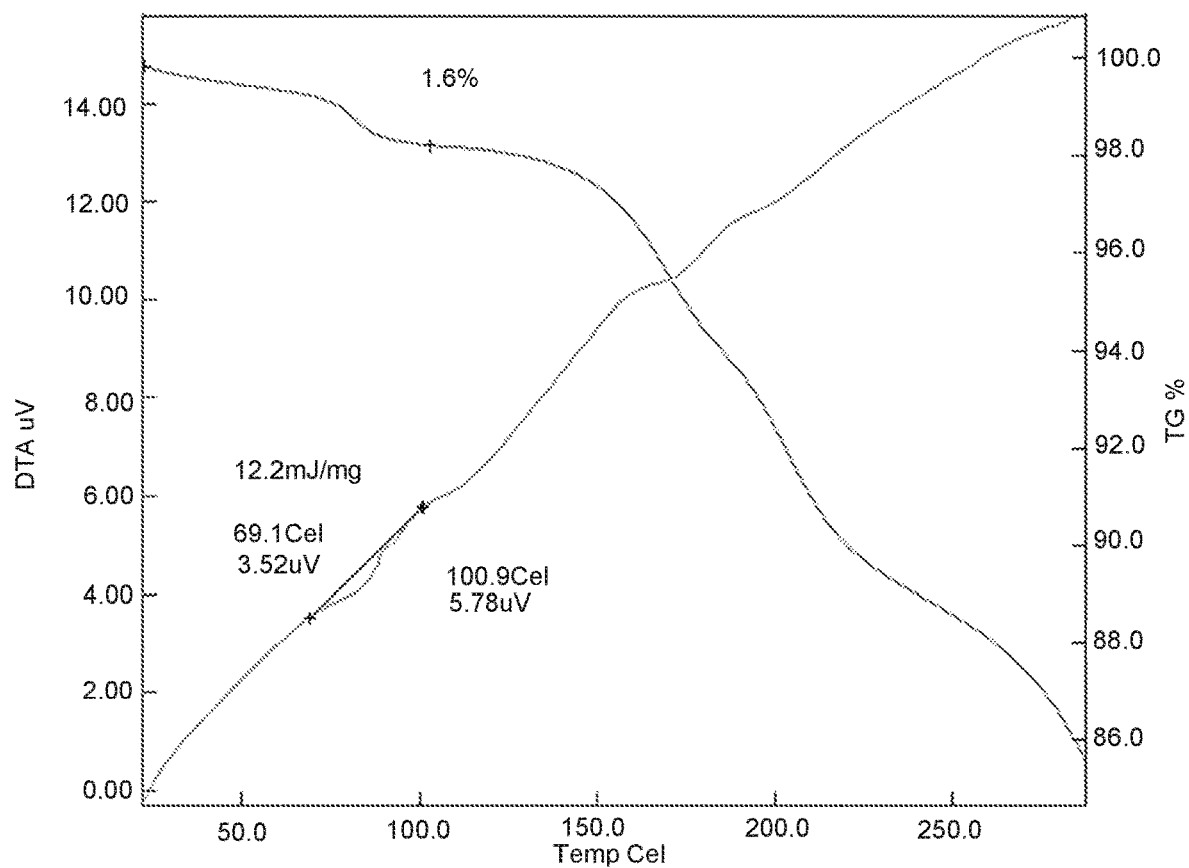
FIG. 3 is a TG/DTA thermogram of amorphous compound 1 hydrochloride.
Figure 4:
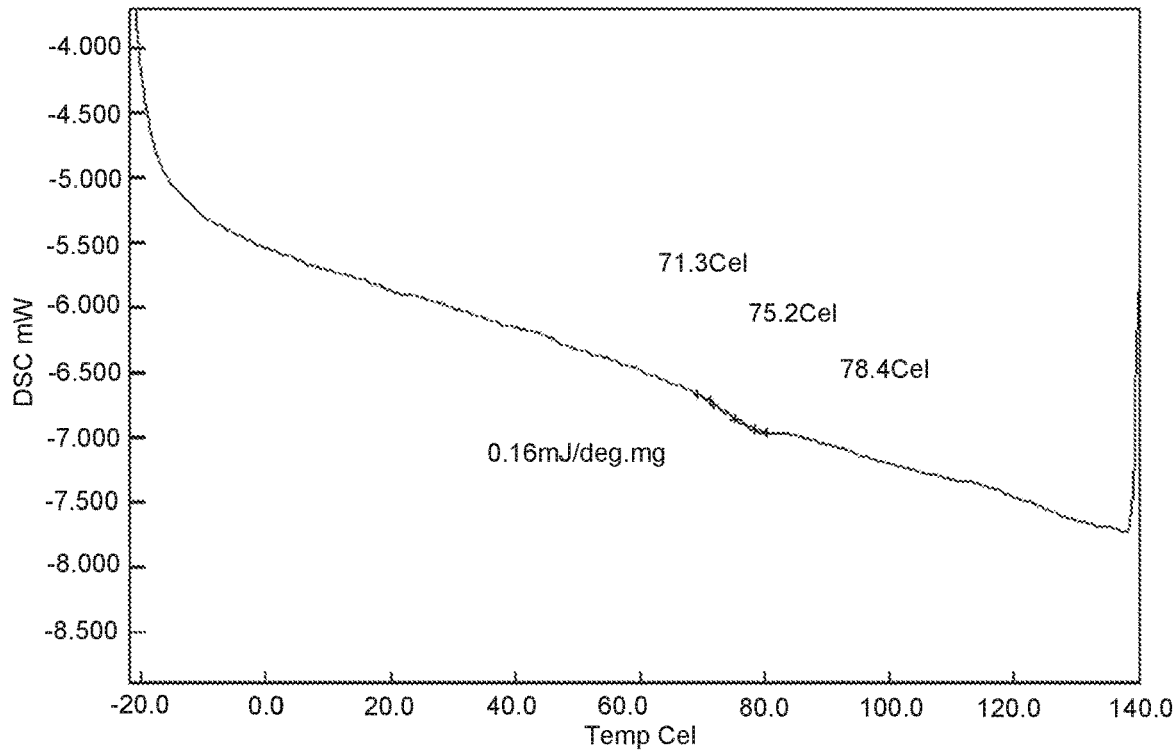
FIG. 4 is a DSC thermogram of amorphous compound 1 hydrochloride.
Figure 5:
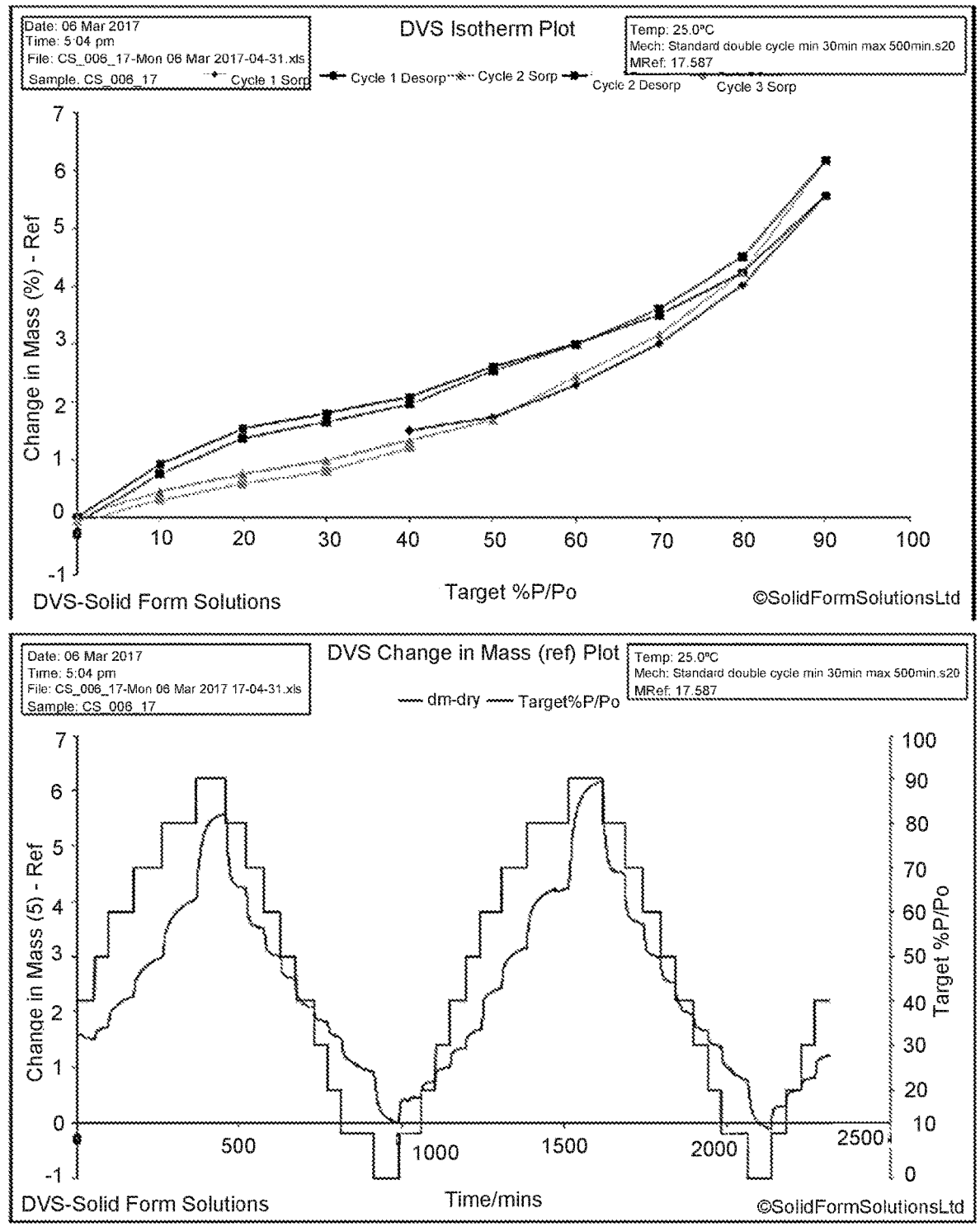
FIG. 5 is a DVS plot of amorphous compound 1 hydrochloride.
Figure 6:
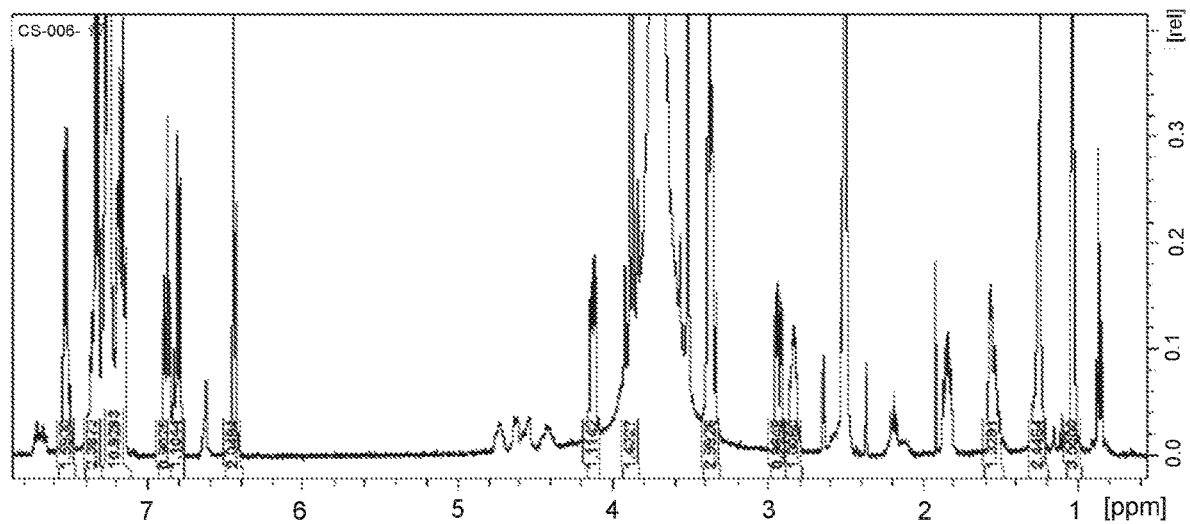
FIG. 6 is a NMR spectrum of amorphous compound 1 hydrochloride.
Figure 7:
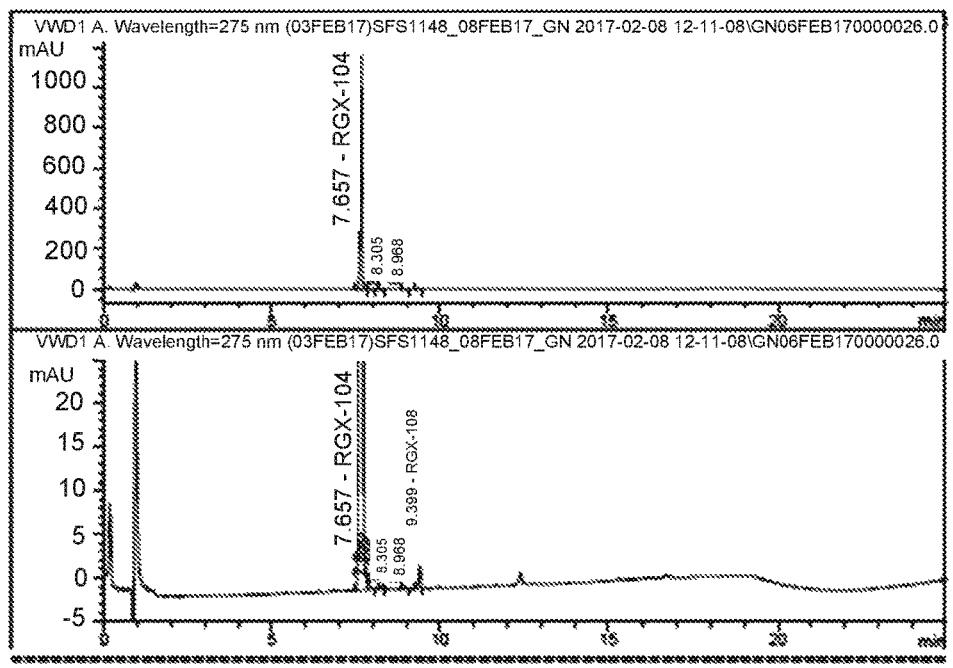
FIG. 7 is a HPLC chromatogram of amorphous compound 1 hydrochloride.

Amorphous HCl salt was characterized by XRPD (FIG. 1), PLM (FIG. 2), TG/DTA (FIG. 3), DSC (FIG. 4), DVS (FIG. 5), NMR (FIG. 6), and HPLC-UV (FIG. 7) following the methods described in Example 1. Characterization of the amorphous material yielded the following information:

The amorphous material was amorphous by XRPD analysis.

The amorphous material was nonbirefringent by PLM analysis, with no clearly defined morphology.

TG analysis of the amorphous material showed a weight loss of about 1.6% from the outset up to about 101° C. corresponding to an endothermic event in the DTA between about 69° C. to about 101° C.

DSC analysis of the amorphous material showed a small thermal event between 70° C. to 80° C.

DVS analysis of the amorphous material indicated that it appears to be highly hygroscopic with a mass uptake of about 6.17% at 90% RH. No change in the solid form was observed during the DVS analysis. The post-DVS sample remained amorphous.

The purity of the amorphous material was found to be 99.58% by HPLC analysis.

Example 3. Preparation of Crystalline Form 1

Approximately 1 g of amorphous, hydrochloride salt of compound 1 was added to a 20 mL glass vial. 2.5 mL of 2-propanol was added at about 22° C. and stirred. A clear solution was observed. Crystallization of solid material was observed. 6 mL of diisopropylether (DIPE) was added as an anti-solvent. Further crystallization of material was observed. After stirring at about 22° C. for 1 hour, the mixture was cooled down to about 5° C. at 0.25° C./minute. The solids were filtered over a Buchner funnel (3 cm diameter) using Whatman grade 1 filter paper. Isolated material was dried under vacuum at ambient temperature (about 22° C.) for about 20 hours. The material was then dried under vacuum at 40° C. after about 66 hours, then further dried at about 45° C. for about 24 hours.

Figure 8:
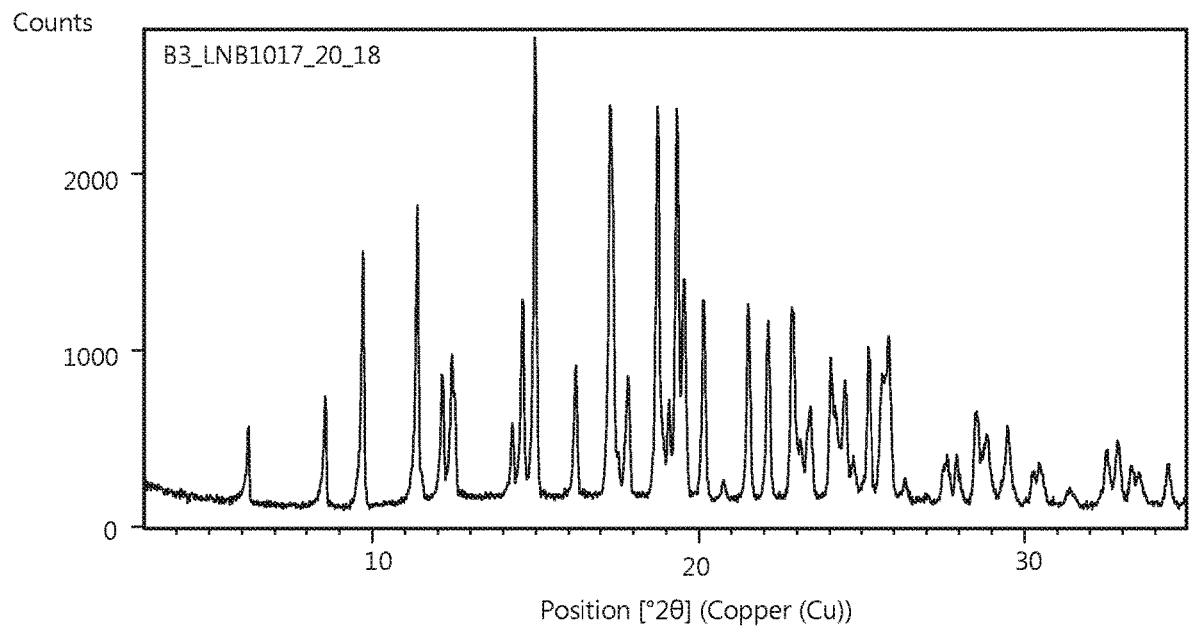
FIG. 8 is an XRPD diffractogram of Form 1.

Material was observed to be crystalline by XRPD (FIG. 8) and the form was designated as Form 1. Form 1 was also isolated from 2-propanol/heptane solvent system via a cooling followed by anti-solvent addition crystallization. No change in the crystalline pattern was observed during the drying process at 22° C., 40° C., and then at 45° C. During drying, some loss in the crystallinity was also observed. TGA of material dried at ambient temperature (about 22° C.) under vacuum for 20 hours showed a weight loss of about 6.3% from the outset up to about 108° C. An endothermic event was observed to be associated with this weight loss at an onset of 81° C. (peak at 93° C.) in the DTA. Further decomposition of material was then observed. TGA of material dried at about 40° C. under vacuum for about 66 hours showed a weight loss of about 2.7% from the outset up to about 104° C. An endothermic event was observed associated with this weight loss at an onset of about 80° C. (peak at about 92° C.) in the DTA. Further decomposition of material was then observed. TGA of material dried at about 45° C. under vacuum for about 24 hours showed a weight loss of about 1.6% from the outset up to about 102° C. An endothermic event was observed associated with this weight loss at an onset of about 82° C. (peak at about 91° C.) in the DTA. Further decomposition of material was then observed.

Example 4. Preparation of Crystalline Form 2

Approximately 99 mg of amorphous, hydrochloride salt of compound 1 was added to a 2 mL glass vial and dissolved in about 250 μL of 2-propanol at about 22° C. To the mixture, about 1.3 mL of MTBE was added and the mixture stirred at about 22° C. for 4 hours. The mixture was cooled to about 5° C. at 0.1° C./minute and stirred at about 5° C. for about 16 hours. The solid was isolated by centrifugation using a 0.22 μm nylon filter tube. The material was dried for about 64 hours under vacuum at about 22° C. The isolated material was crystalline by XRPD and designated as Form 2. After drying, TGA showed a weight loss of about 8.3% from the outset up to about 120° C. An endothermic event was observed associated with this weight loss at an onset of 92° C. (peak at 97° C.) in the DTA. Further decomposition of material was then observed.

In a separate preparation, approximately 1 g of amorphous, hydrochloride salt of compound 1 was added to a 20 mL glass vial. 1.5 mL of THF was added at about 22° C. A clear solution was observed. 5 mL of diisopropylether (DIPE) was added as an anti-solvent. After stirring at about 22° C. for 1 hour, the mixture was cooled down to about 5° C. at 0.25° C./minute. The mixture was stirred at 5° C. for about 16 hours. The solids were collected, under vacuum, using a Buchner funnel with Whatman grade 1 filter paper. Isolated material was dried under vacuum at ambient temperature (about 22° C.) for about 5 hours. The material was then further dried under vacuum at 40° C. for about 66 hours, then dried at about 45° C. for about 24 hours.

Figure 9:
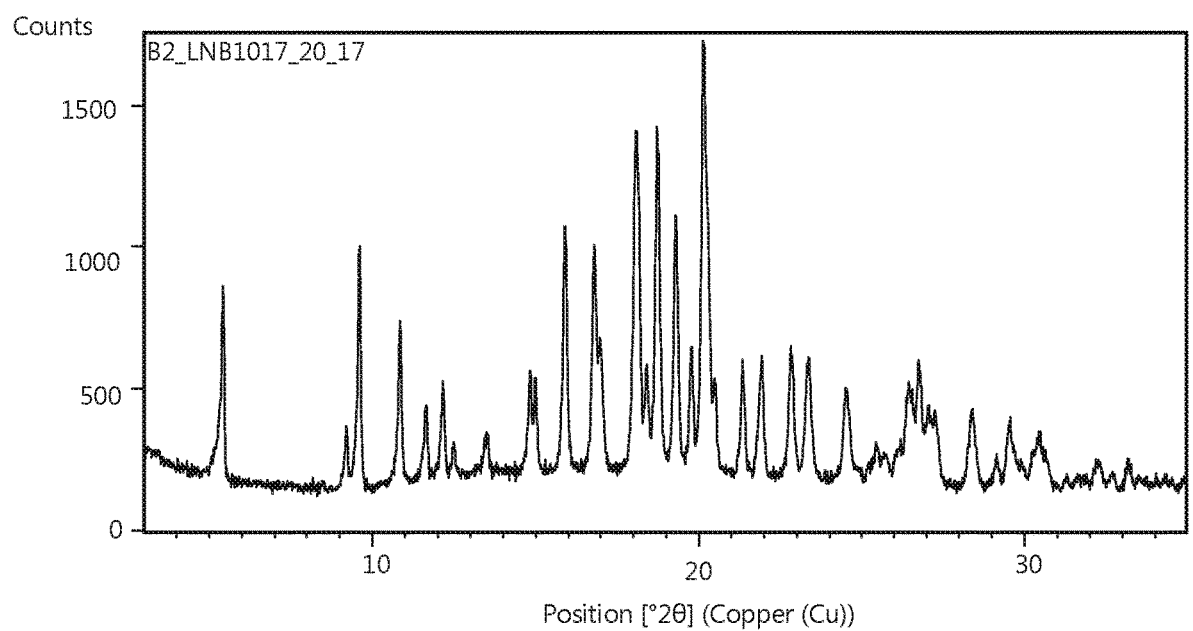
FIG. 9 is an XRPD diffractogram of Form 2.

The isolated wet material was crystalline by XRPD (FIG. 9) and designated as Form 2. During the drying process at 22° C. and 40° C., the solid was consistent with Form 2. After drying at 45° C., predominately Form 2 with some extra peaks were observed by XRPD. During drying, some loss in the crystallinity was also observed. TGA of material dried at about 45° C. under vacuum for about 24 hours showed a weight loss of about 0.5% from the outset up to about 100° C. An endothermic event was observed associated with this weight loss at an onset of about 76° C. (peak at about 96° C.) in the DTA. Further decomposition of material was then observed.

Example 5. Preparation of Crystalline Form 4

Approximately 2 g of amorphous, hydrochloride salt of compound 1 was added to a 20 mL glass vial. 3 mL of THF was added at 22° C., mixed with an octahedral magnetic needle. A clear solution was obtained. After addition of 100 μL of DIPE as anti-solvent, the mixture was seeded using Form 2 material (about 2%). Stirred for 30 minutes. DIPE was further added in 100 μL aliquots to a total of 10 mL of DIPE and the mixture was stirred at about 22° C. for 1 hour. The mixture was then cooled down to 5° C. at 0.19° C./minute. After stirring at 5° C. for 10 minutes, the slurry was filtered, under vacuum, using a Buchner funnel and Whatman filter paper no. 1. The wet material was dried under vacuum on the filter for 30 minutes. Material was observed to be crystalline by XRPD and consistent with Form 2.

Figure 10:
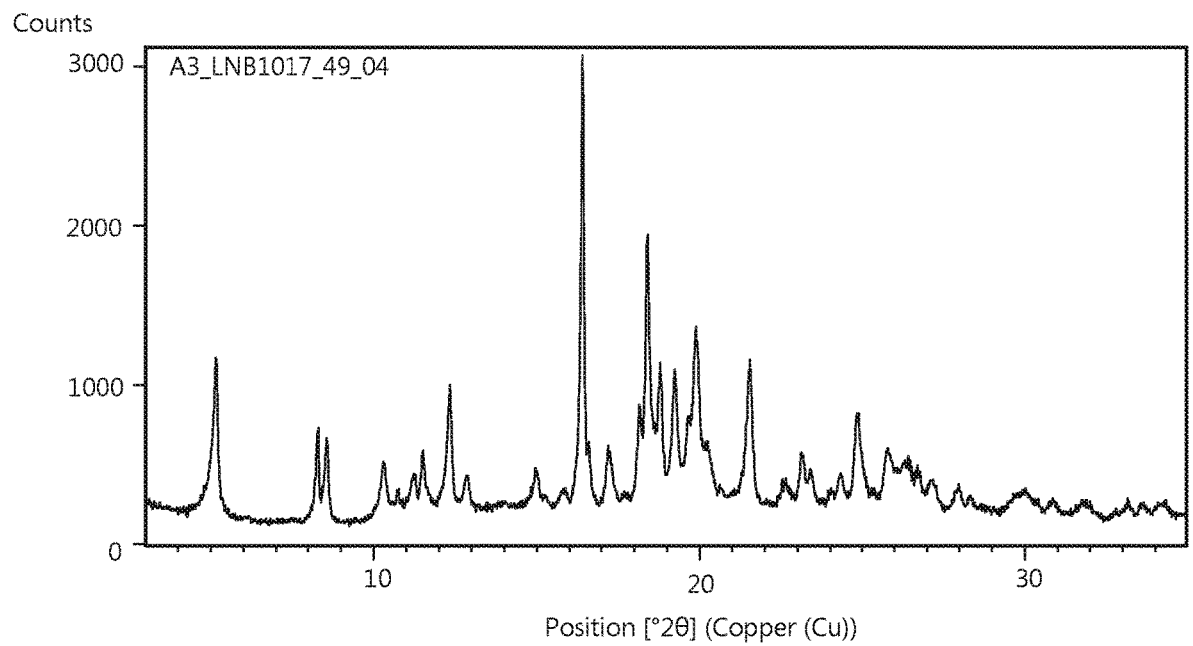
FIG. 10 is an XRPD diffractogram of Form 3.

Approximately 1 g of wet Form 2 material was added to a 20 mL glass vial. About 6 mL of toluene was added at ambient (about 22° C.) to make a slurry. After stirring at about 22° C. for about 64 hours, the slurry was cooled down to about 5° C. at 0.2° C./minute and further stirred at 5° C. for about 1 hour. The slurry was filtered, under vacuum, using a Buchner funnel and Whatman filter paper no. 1. Form 2 material was converted to Form 3 by slurrying in toluene as confirmed by XRPD analysis (FIG. 10). TG analysis on wet material (Form 3) showed a weight loss of about 11.46% from the outset up to about 66° C. A broad/shallow endotherm in the DTA between 39° C. to 66° C. was observed associated with this weight loss. A further weight loss of 2.08% was also observed in the TGA with a broad and shallow endotherm in the DTA between 69° C. to 108° C.

Figure 11:
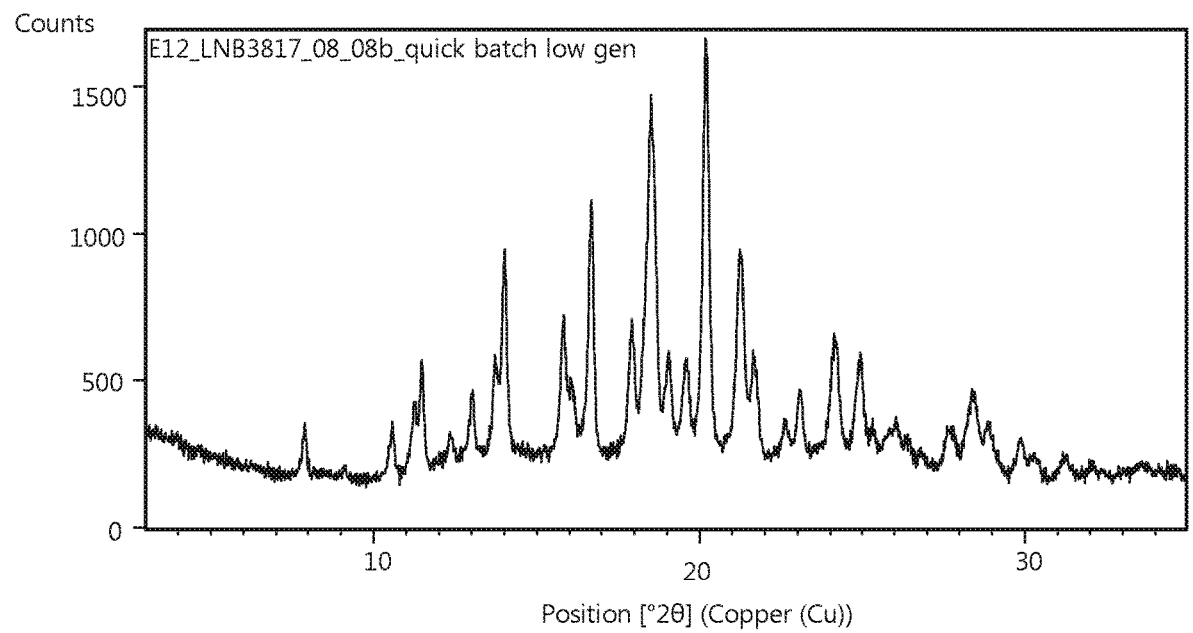
FIG. 11 is an XRPD diffractogram of Form 4.
Figure 12:
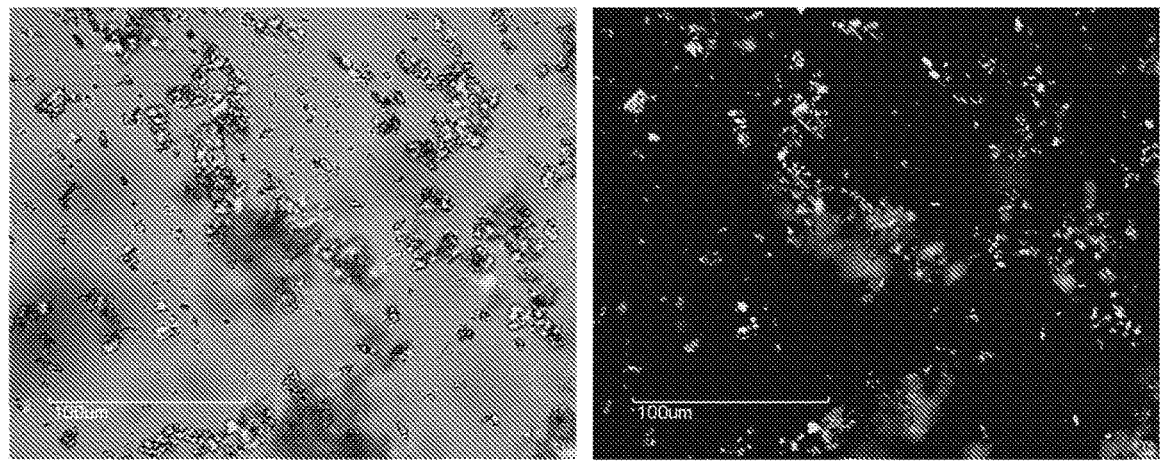
FIG. 12 is a PLM image of Form 4.
Figure 14:
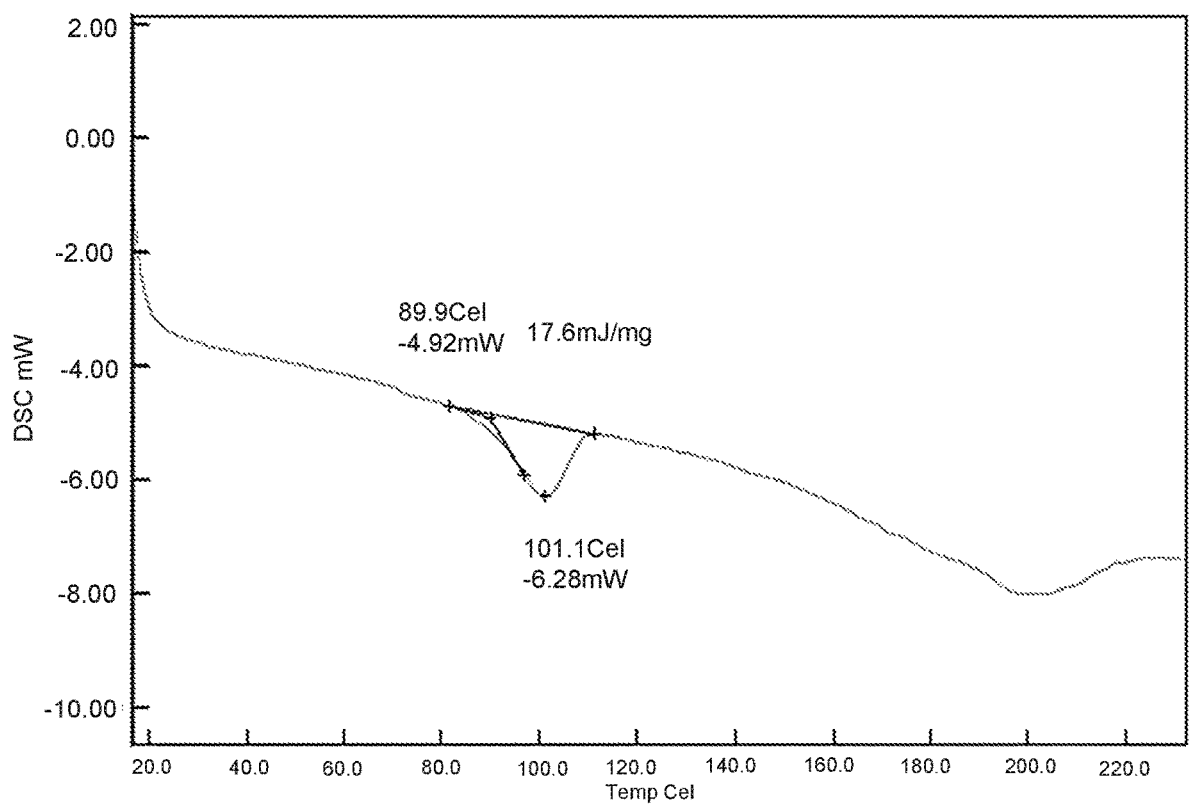
FIG. 14 is a DSC thermogram of Form 4.

Form 3 material is converted to Form 4 by drying as follows. Wet, Form 3 material was dried at about 45° C. under vacuum for approximately 22 hours. The dried material was equilibrated at ambient temperature for about 16 hours. The dried material was characterized by XRPD, PLM, TG/DTA, DSC, DVS, KF and HPLC-UV. PLM (FIG. 12) showed small, birefringent particles with no clearly defined morphology. The crystalline material had a XRPD pattern consistent with Form 4 (FIG. 11). TG analysis showed a weight loss of about 0.6% from the outset up to about 114° C. An endothermic event was observed associated with this weight loss at an onset of about 88° C. (peak at about 99° C.) in the DTA. Further decomposition of material was then observed. DSC analysis (FIG. 14) showed an endothermic event at an onset of about 89.9° C. (peak at about 101° C.). Water content was measured by KF analysis to be 0.8% water.

Figure 15:
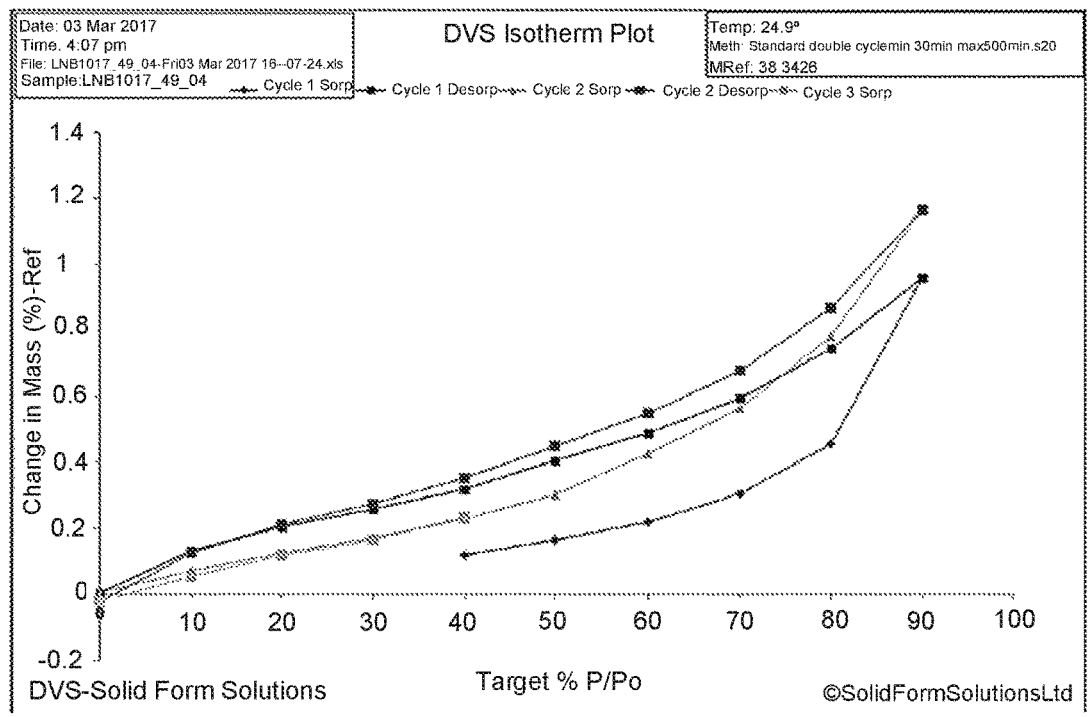
FIG. 15 is a DVS plot of Form 4.

The Form 4 material (isolated from Form 2 slurried in toluene) appears to be slightly hygroscopic with a mass uptake of about 1.16% at 90% RH by DVS analysis, but is much less hygroscopic than the amorphous compound which had a mass uptake of about 6.17% at 90% RH by DVS analysis (FIG. 15). XRPD analysis on the post-DVS sample showed no change in the solid form, Form 4 was observed. The dried material showed a purity of 99.5% by HPLC and GC analysis showed 180 ppm, 17 ppm and 3010 ppm THF, DIPE and Toluene respectively.

Figure 13:
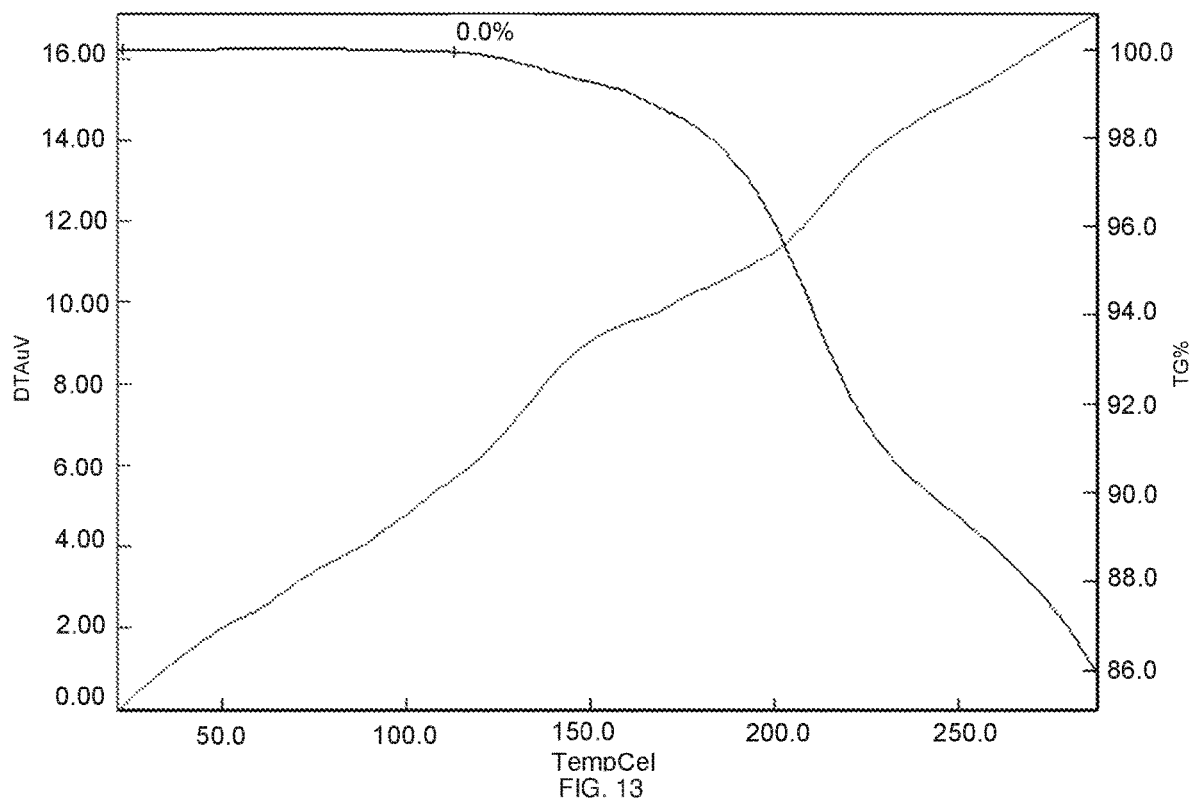
FIG. 13 is a TG/DTA thermogram of Form 4.

A slightly larger preparation, at 2 gm, using an equivalent procedure to generate wet Form 3 material, was dried using a different procedure. This material was dried at about 45° C. under vacuum for approximately 24 hours. TG analysis showed a weight loss of about 1.7% from the outset up to about 115° C. Two endothermic events were observed associated with this weight loss; first endotherm at an onset of about 73° C. and the second one at an onset of about 88° C. in the DTA. Further decomposition of material was then observed. The material was further dried at about 40° C. for 65 hours. A free-flowing solid was obtained. TG analysis revealed a weight loss of about 0.5 wt. % from the outset up to about 112° C. An endothermic event was observed associated with this weight loss at an onset of about 70° C. (peak at about 87° C.) in the DTA. Further decomposition of material was then observed. Residual toluene of 4881 ppm was observed by GC analysis, DIPE and THF were not detected. Material was observed to be 99.9 area % pure by HPLC analysis. The obtained material was further dried at about 45° C. for 112 hours. After drying, the material was analyzed by XRPD, TG/DTA, and GC. Crystallinity of the material remained intact. No weight loss was observed by TG analysis up to about 115° C. Decomposition of the material was observed after about 115° C. (FIG. 13). The material appears to be anhydrous by TG/DTA. Residual toluene was observed to be 841 ppm by GC. Drying of Form 3 material to produce Form 4 material, an ansolvate, was shown to be successful.

Example 6. Preparation of Crystalline Form 5

Approximately 50 mg of Form 4, hydrochloride salt of compound 1 was dissolved in 200 μL of anisole at ca 22° C. in a 2 mL vial. The resulting clear solution was stirred at about 22° C. for 4 hours then cooled down to about 5° C. at 0.1° C./minute. The mixture was temperature cycled between about 5° C. and about 22° C. at 0.1° C./minute, with a hold of 1 hour at about 5° C. and about 22° C. during each cycle, for about 90 hours. A slurry was observed and the material was isolated by centrifugation using a 0.22 µm nylon filter. The isolated (wet) material was dried under vacuum at about 40 to about 45° C. for about 20 hours. The dried material was analyzed by XRPD and confirmed as Form 5.

A larger preparation was carried out where approximately 1 g of amorphous, hydrochloride salt of compound 1 was added to a 20 mL vial. 4.0 mL of anisole was added at about 22° C. The vial was stirred, then sonicated for 15 minutes. Slightly turbid solution was observed. The experiment was seeded using Form 5 material. The seed persisted, the experiment was stirred at about 22° C. for 4 hours, then cooled down to about 5° C. at 0.1° C./minute. The experiment was temperature cycled between 5° C. and 22° C. at 0.1° C./minute, with a hold of 1 hour at 5° C. and 22° C. during each cycle. Temperature cycled for 1 cycle. A gel-like material was observed. Heptane was added in 100 µL aliquots at about 22° C., until a total of 1 mL of heptane was added. The experiment was stirred at about 22° C. for 4 hours then cooled down to about 5° C. at 0.1° C./minute. The experiment was temperature cycled between 5° C. and 22° C. at 0.1° C./minute, with a hold of 1 hour at 5° C. and 22° C. during each cycle. Temperature cycled for 1 cycle. A non-filterable, gel-like material was observed at about 5° C. The material was isolated by decanting the solvent and the material was dried under nitrogen at about 5° C. for 2 hours where white solid material was observed. The wet material was dried at about 30-35° C. for 65 hours under vacuum, then at about 40° C. to 45° C. for about 168 h under vacuum.

Figure 16:
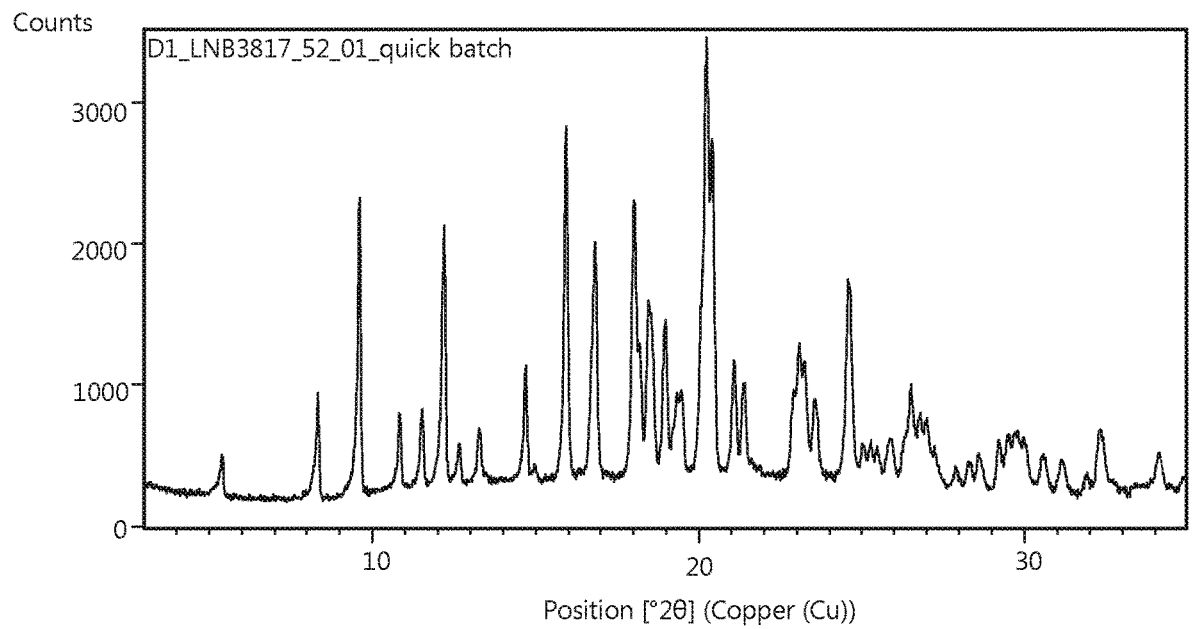
FIG. 16 is an XRPD diffractogram of Form 5.

The final material was analyzed by DSC, DVS, PLM, HPLC-UV and GC. XRPD analysis showed the isolated filtered material to be consistent with Form 5 (FIG. 16). A 0.5% weight loss was observed by TGA and an endothermic event was observed associated with this weight loss at an onset of about 72° C. (peak at about 76° C.) in the DTA. Decomposition of material was observed at higher temperatures. No significant loss in the crystallinity of the material was observed during drying, by XRPD analysis. DSC thermogram showed an endothermic event at an onset of about 69° C. (peak at about 74° C.). The dried Form 5 material showed about 0.7 wt. % water by KF analysis and a purity of 99.9% by HPLC analysis. DVS analysis on the Form 5 material showed it to be slightly hygroscopic with a mass uptake of about 2.7% at 90% RH. XRPD analysis on the post-DVS sample showed the solid to be partially amorphous Form 5 material. PLM showed the Form 5 particles to be birefringent with no clearly defined morphology. GC residual solvent analysis showed the anisole content to be 8.2 wt. % even after drying. The Form 5 material is therefore considered to be a solvate.

Example 7. Preparation of Crystalline Form 6

Approximately 25 mg of Form 4, hydrochloride salt of compound 1 was dissolved in 90 µL of 1-Butanol at about 22° C. in a 2 ml vial. The mixture was placed at about 5° C., resulting in a slurry being obtained. XRPD analysis was carried out on the resulting solids and the crystalline form assigned as Form 6.

Figure 17:
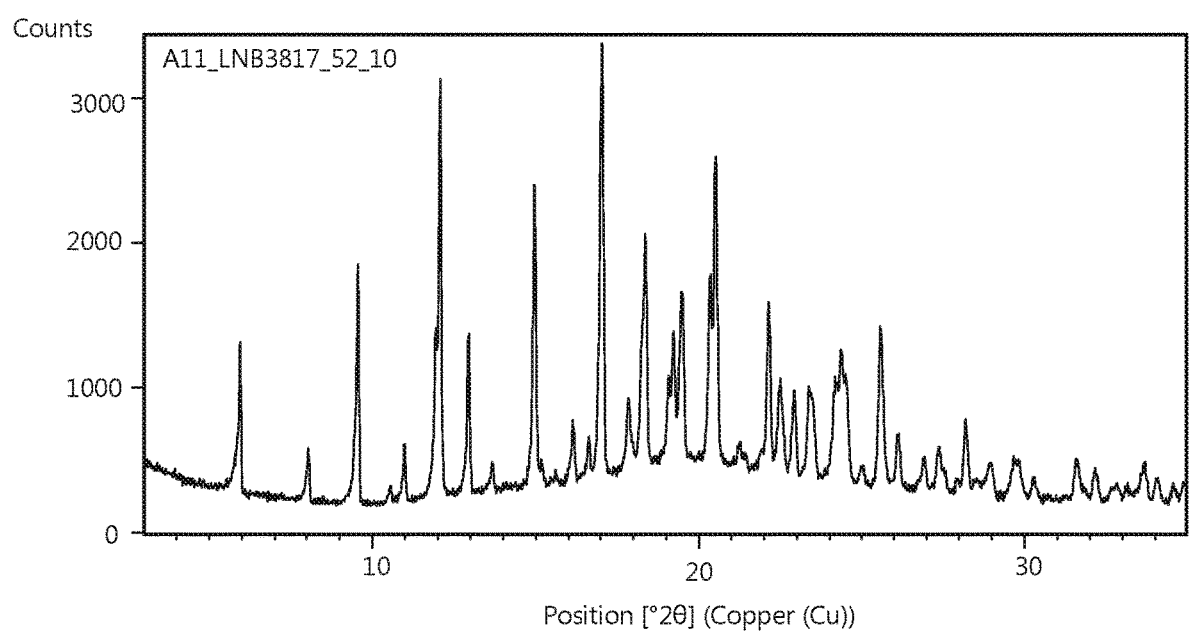
FIG. 17 is an XRPD diffractogram of Form 6.

A larger preparation was carried out where approximately 1 g of amorphous, hydrochloride salt of compound 1 was added to a 20 mL vial. 2 mL of 1-Butanol was added at about 22° C. and the resultant clear solution was stirred. To the experiment, 0.5 mL of heptane was added and the experiment was seeded using Form 6 material. The experiment was stirred at about 22° C. for 4 hours then cooled down to about 5° C. at 0.1° C./minute. The experiment was temperature cycled between 5° C. and 22° C. at 0.1° C./minute with a hold of 1 hour at 5° C. and 22° C. during each cycle. Temperature cycled for about 16 hours. To the experiment, 1.5 mL heptane was added at about 22° C. and the experiment was further stirred for 5 hours. The solids were isolated by filtering over a Buchner funnel. The material was dried over filter for 10 minutes. The wet material was dried at 40-45° C. under vacuum for about 20 hours, followed by drying at 30-35° C. under vacuum for about 65 hours, followed by drying at 40-45° C. under vacuum for about 192 h. After completion of the drying process, the final sample was analyzed by DSC, DVS, PLM, HPLC-UV and GC. XRPD analysis showed the isolated filtered material to be consistent with Form 6 (FIG. 17). A weight loss of 0.3% was measured by TGA. An endothermic event was observed associated with this weight loss at an onset of about 76° C. (peak at about 81° C.) in the DTA. Decomposition of material was observed at higher temperatures. No significant loss in the crystallinity of the material was observed during drying, by XRPD analysis. DSC thermogram showed an endothermic event at an onset of about 71° C. (peak at about 76° C.). The dried Form 6 material showed about 0.8 wt. % water by KF analysis and a purity of 98.6% by HPLC analysis. DVS analysis on the Form 6 material showed it to be slightly hygroscopic with a mass uptake of about 2.3% at 90% RH. XRPD analysis on the post-DVS sample showed no significant change in the solid form, Form 6 was observed. PLM showed the Form 6 particles to be birefringent with no clearly defined morphology. GC residual solvent analysis indicated the 1-butanol content to be 2.3 wt. % even after drying.

Example 8. Preparation of Crystalline Form 7

Figure 18:
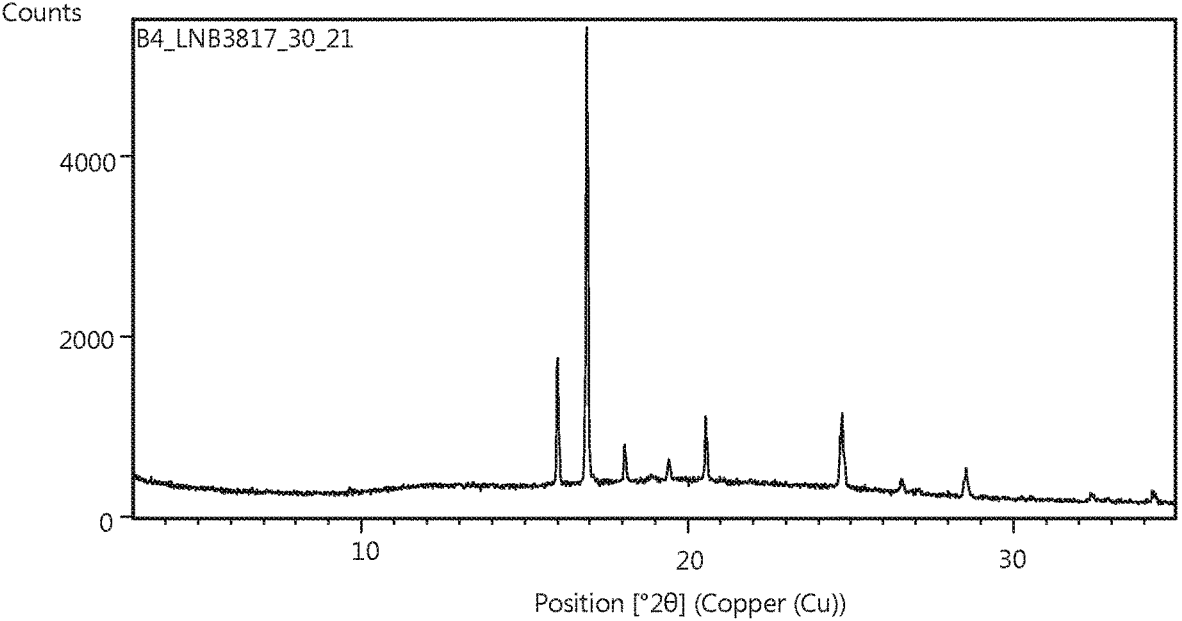
FIG. 18 is an XRPD diffractogram of Form 7.

Approximately 26 mg of Form 4, hydrochloride salt of compound 1 was dissolved in 60 µL of THF at about 22° C. in a 2 mL vial. The mixture was placed at about 5° C. To the mixture, about 300 µL of heptane was added as an antisolvent at about 5° C. The mixture was stirred at about 5° C. for about 16 hours. A slurry was observed and the material was isolated by centrifugation using a 0.22 µm nylon filter. The solid was analyzed by XRPD (FIG. 18). The crystalline form was assigned as Form 7.

Example 9. Preparation of Crystalline Forms 8 and 9

A competitive slurry technique was used to assess polymorph stability. About 8 mg of each of Form 4 and 5 material or Form 4 and 6 material or Form 5 and 6 material was combined in 2 mL vials. Vials were placed into temperature controlled blocks and stirred at about 20 or about 40° C. 200-500 µL of heptane, cyclohexane, xylene or cumene was added to the experiment at about 20 or about 40° C. to make a slurry. The experiments were stirred at 20 or 40° C. for about 64 hours. Samples vortex mixed to re-slurry solids as required. Slurries were filtered by centrifugation using 0.2 µm filter tubes. Isolated solids were analyzed by XRPD.

Competitive slurring of Form 4, Form 5 and Form 6 experiments showed the following:
Heptane slurries produced partially crystalline Form 5 and Form 6 or Form 4 and 5 or amorphous materials.

Cyclohexane slurries produced Form 8 or partially crystalline Form 8 or Form 5 materials.

Figure 20:
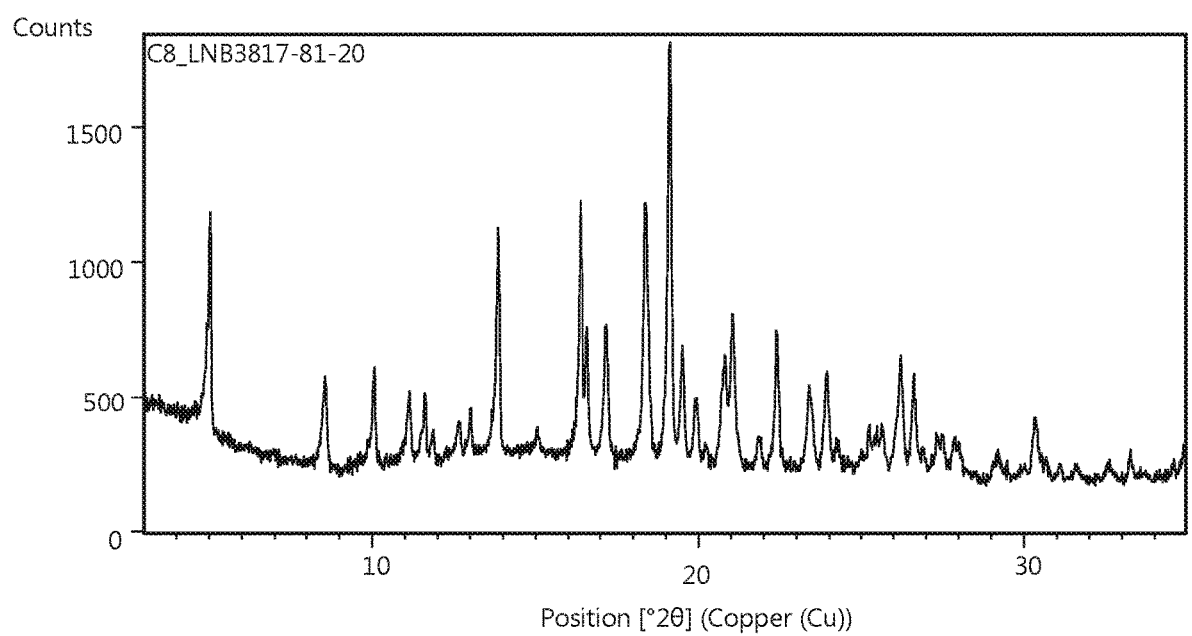
FIG. 20 is an XRPD diffractogram of Form 9.

Xylene slurries produced Form 9 or Form 3 or amorphous materials. The XRPD diffractogram from solids obtained by slurrying Form 5 and Form 6 together in cumene at 40° C. for about 64 hours is shown in FIG. 20.

Cumene slurries produced a new Form 9 or amorphous materials.

Figure 19:
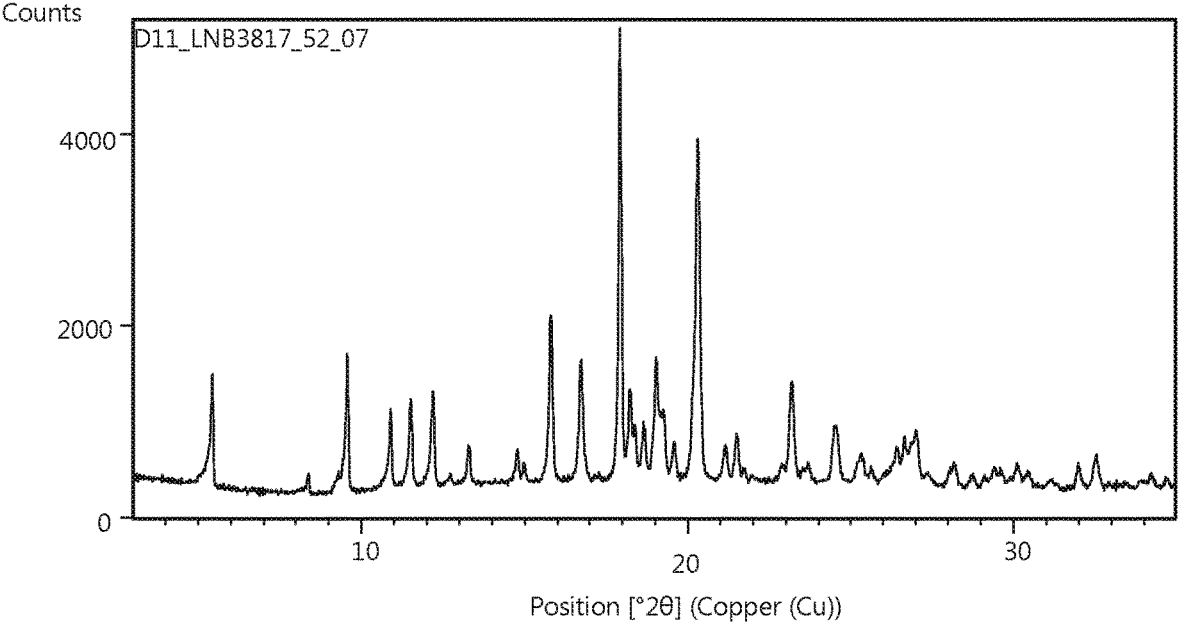
FIG. 19 is an XRPD diffractogram of Form 8.

Form 8 solids were also isolated using several different solvent systems, including MEK/heptane, MEK/cyclohexane and 1-propanol/cyclohexane via a cooling/anti-solvent addition technique. For MEK/cyclohexane, approximately 56 mg of Form 4, hydrochloride salt of compound 1 was dissolved in 80 μL of MEK at about 22° C. in a 2 ml vial. To the solution, about 400 μL of cyclohexane was added in 20 μL aliquots at about 22° C. The mixture was stirred at about 22° C. for 4 hours and then cooled to about 5° C. at 0.1° C./minute. The mixture was then temperature cycled between about 5° C. and 22° C. at 0.1° C./minute with a hold of 1 hour at 5° C. and 22° C. during each cycle. Temperature cycled for about 90 hours. A slurry was observed and the material was isolated by centrifugation using a 0.22 μm nylon filter. The isolated solid was dried under vacuum at about 40 to 45° C. for 38 hours. The solids prepared in MEK/cyclohexane showed a XRPD diffractogram consistent with Form 8 (FIG. 19). After drying under vacuum at 40-45° C. for 38 h in total, a weight loss of about 5.5% from the outset up to about 115° C., was detected by TGA. An endothermic event was observed associated with this weight loss at an onset of about 93° C. (peak at about 100° C.) in the DTA. Further decomposition of material was then observed. GC residual solvents analysis indicated the material to contain about 2.1 wt. % MEK and 7.7 wt. % cyclohexane.

Several isolated solids of Form 9 from the competitive slurry experiments were combined and re-tested by XRPD analysis confirming Form 9. TGA of the combined sample showed a weight loss of about 2.9% from the outset up to about 94° C. An endothermic event was observed at an onset of about 80° C. (peak at about 87° C.) in the DTA. Further decomposition of material was then observed. After drying at 40-45° C., XRPD showed a slight decrease in crystallinity and small changes were observed in the XRPD pattern. The dried material showed about 1% weight loss up to 102° C. by TGA. An endothermic event was detected with onset at about 69° C. (peak at about 74° C.) by DTA. Further decomposition of material was then observed.

Example 10—Manufacturing of Capsules

The manufacturing process begins with melting Maisine 35-1. The liquid Maisine 35-1 is then added to a stainless steel mixing kettle that has been heated to 40-45° C. The sodium oleate, pre-screened through 20 mesh hand screen, is added, and the mixture is stirred at 40-45° C. for a minimum of 30 minutes. Disodium EDTA and sodium citrate are added slowly to prevent agglomeration, and the mixture is stirred at 40-45° C. for a minimum of 30 minutes. Next, the crystalline ansolvate of the hydrochloride salt (Form 4) is added, and the suspension is stirred at 40-45° C. overnight. Gelucire 44-14, which had also been pre-melted, is added to the mixture with stirring. The resultant blend is stirred for at least 20 minutes at 40-45° C. The formulation remains slightly turbid (presumed to be finely dispersed sodium chloride). In-process samples are taken before the mixture is encapsulated.

The hot, bulk blend is transferred to the encapsulation hopper with in-line filtration through a 100-mesh screen. Standard opaque white hard gelatin capsules are filled with the liquid blend at 40-45° C. The capsules are then banded using a gelatin/Polysorbate 80 banding solution, cooled to ambient temperature, and then dried for at least 12 hours. Capsules are sorted by weight, visually inspected and passed through a metal detector before being transferred into fiber drums. The bulk capsules are filled into HDPE bottles, capped, and induction-sealed, and the caps are then re-torqued to engage the child-resistant feature. The current storage condition is 2 to 8° C.

OTHER EMBODIMENTS

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

While the methods have been described in conjunction with various embodiments and examples, it is not intended that the methods be limited to such embodiments or examples. On the contrary, the present disclosure encompasses various alternatives, modifications, and equivalents, as will be appreciated by those of skill in the art.

While the methods have been particularly shown and described with reference to specific illustrative embodiments, it should be understood that various changes in form and detail may be made without departing from the spirit and scope of the present disclosure. Therefore, all embodiments that come within the scope and spirit of the present disclosure, and equivalents thereto, are intended to be claimed. The claims, descriptions and diagrams of the methods, systems, and assays of the present disclosure should not be read as limited to the described order of elements unless stated to that effect.

What is claimed is:

1. A crystalline ansolvate of the hydrochloride salt of a compound having the structure:

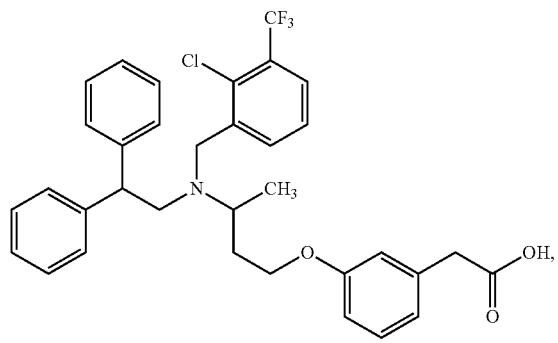

wherein the crystalline ansolvate has peaks at diffraction angle 2θ (°) of 9.7°±0.5, 11.4°±0.5, 15.0°±0.5, 17.3°±0.5, 18.8°±0.5, and 19.3°±0.5 as measured by X-ray diffractometry or calculated from X-ray diffractometry.

2. The crystalline ansolvate of claim 1, wherein the crystalline ansolvate is substantially free of a solvated polymorph of the compound.

3. The crystalline ansolvate of claim 2 having a loss of weight from 25° C. to 140° C. of less than 1% as measured by thermal gravimetric analysis.

4. The crystalline ansolvate of claim 2 having an endothermic onset at about 90° C. in differential scanning calorimetry (DSC) profile.

5. A method of producing a pharmaceutical composition comprising a compound having the structure:

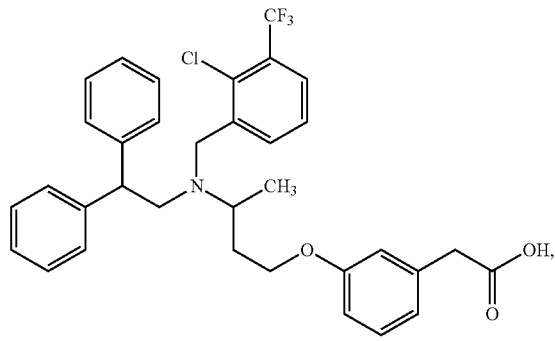 [SMILES: CC(CCOc1cccc(CC(=O)O)c1)N(Cc1cccc(C(F)(F)F)c1Cl)CC(c1ccccc1)c1ccccc1]

or a pharmaceutically acceptable salt thereof, the method comprising mixing (i) a lipophilic vehicle, comprising a lipid excipient, and (ii) the crystalline ansolvate of claim 1, wherein the lipophilic excipient is selected from fatty acids, glycerol fatty acid esters, and surfactants.

6. A pharmaceutical composition produced by the method of claim 5, and a pharmaceutically acceptable excipient.

7. A method of modulating LXRβ activity, the method comprising administering an effective amount of the pharmaceutical composition of claim 6, or the crystalline ansolvate of claim 1.

8. The method of claim 7, wherein LXRβ activity is modulated in a subject having cancer, and wherein the cancer is breast cancer, colon cancer, renal cell cancer, lung cancer, hepatocellular carcinoma, gastric cancer, ovarian cancer, pancreatic cancer, esophageal cancer, prostate cancer, sarcoma, bladder cancer, head and neck cancer, glioblastoma, diffuse large B-cell lymphoma, leukemia, or melanoma.

9. The method of claim 8, wherein the cancer is metastatic cancer.

* * * * *